US00RE43550E

(19) United States
(12) Reissued Patent
Moore et al.

(10) Patent Number: US RE43,550 E
(45) Date of Reissued Patent: Jul. 24, 2012

(54) METHODS FOR COLLECTING FEES FOR HEALTHCARE MANAGEMENT GROUP

(75) Inventors: Terrance Moore, Oviedo, FL (US); Charles Lewis, Lake Mary, FL (US)

(73) Assignee: Jasos Intellectual Property LLC, Lake Mary, FL (US)

(21) Appl. No.: 12/837,290

(22) Filed: Jul. 15, 2010

Related U.S. Patent Documents

Reissue of:
(64) Patent No.: 7,401,027
Issued: Jul. 15, 2008
Appl. No.: 09/812,703
Filed: Mar. 19, 2001

(51) Int. Cl.
*G06Q 10/00* (2006.01)
*G06Q 50/00* (2006.01)
*G06Q 40/00* (2006.01)

(52) U.S. Cl. ..... 705/2; 705/4; 705/3; 705/40; 705/53; 705/910; 600/300

(58) Field of Classification Search ..... 705/2–4, 705/11, 35, 53, 40; 707/100, 769, 776
See application file for complete search history.

(56) References Cited

U.S. PATENT DOCUMENTS 5,365,425 A 11/1994 Torma
5,535,118 A * 7/1996 Chumbley ..... 235/375
5,557,514 A 9/1996 Seare
5,706,441 A * 1/1998 Lockwood ..... 705/3
5,722,416 A 3/1998 Swanson
5,722,418 A 3/1998 Bro
5,724,379 A * 3/1998 Perkins et al. ..... 705/2
5,737,539 A 4/1998 Edelson et al.
5,784,635 A * 7/1998 McCallum ..... 712/32
5,835,897 A 11/1998 Dang
5,918,208 A 6/1999 Javitt
5,924,073 A 7/1999 Tyuluman
5,953,704 A * 9/1999 McIlroy et al. ..... 705/2
6,000,828 A * 12/1999 Leet ..... 705/2
6,012,035 A 1/2000 Freeman
6,014,631 A 1/2000 Teagarden
6,026,364 A 2/2000 Whitworth
6,029,138 A 2/2000 Khorasani
6,055,511 A * 4/2000 Luebbering et al. ..... 705/14.1
6,081,809 A 6/2000 Kumagai
6,112,182 A 8/2000 Akers
6,112,183 A 8/2000 Swanson et al.
6,151,581 A 11/2000 Kraftson (Continued)

OTHER PUBLICATIONS

By Kelly Greene. (Jan. 20, 1999). Ga. Considers Network to Cut Medicaid Costs. Wall Street Journal (Eastern Edition), p. S1. Retrieved May 31, 2011, from ABI/Inform Global. (Document ID: 38172220).*

(Continued)

*Primary Examiner* — Matthew S. Gart
*Assistant Examiner* — Olusegun Goyea
(74) *Attorney, Agent, or Firm* — Bracewell & Giuliani LLP

(57) ABSTRACT

Methods are provided for collecting fees for managing and optimizing the profitability of a plurality of physicians in a healthcare practice participating in an insurance network. The methods include establishing a relationship between a healthcare consultation group and the healthcare practice participating in the insurance network to increase the physician's profitability by reducing a risk of not receiving a predetermined reimbursement amount for ancillary medical costs from the insurance network. The methods also include distributing predetermined percentages of savings attributed to the physicians' modified ancillary medical cost management behavior.

26 Claims, 7 Drawing Sheets

U.S. PATENT DOCUMENTS

| | | | | |
|---|---|---|---|---|
| 6,195,612 | B1 | 2/2001 | Pack-Harris | |
| 6,223,164 | B1 | 4/2001 | Seare | |
| 6,302,844 | B1 | 10/2001 | Walker et al. | |
| 6,370,511 | B1 | 4/2002 | Dang | |
| 6,381,576 | B1 | 4/2002 | Gilbert | |
| 6,385,589 | B1 | 5/2002 | Trusheim | |
| 7,311,666 | B2 * | 12/2007 | Stupp et al. | 600/300 |
| 7,379,885 | B1 | 5/2008 | Zakim | |
| 7,389,245 | B1 * | 6/2008 | Ashford et al. | 705/2 |
| 7,398,217 | B2 | 7/2008 | Lewis | |
| 7,401,027 | B2 * | 7/2008 | Moore et al. | 705/2 |
| 7,426,474 | B2 * | 9/2008 | Schoenbaum et al. | 705/2 |
| 2001/0037216 | A1 | 11/2001 | Oscar | |
| 2001/0041990 | A1 * | 11/2001 | Javitt | 705/2 |
| 2002/0026478 | A1 | 2/2002 | Rodgers et al. | |
| 2002/0111826 | A1 | 8/2002 | Potter | |
| 2002/0120468 | A1 | 8/2002 | Atallah | |
| 2002/0133379 | A1 * | 9/2002 | Lewis et al. | 705/4 |
| 2002/0138303 | A1 | 9/2002 | Enos | |
| 2002/0152097 | A1 * | 10/2002 | Javors | 705/2 |
| 2008/0059248 | A1 | 3/2008 | Lewis | |
| 2008/0097790 | A1 | 4/2008 | Moore | |
| 2008/0243546 | A1 * | 10/2008 | Ashford et al. | 705/2 |
| 2010/0174561 | A1 * | 7/2010 | Moore et al. | 705/3 |

OTHER PUBLICATIONS

Rosenthal, Meredith Beaven (1998). Risk sharing in managed care. Ph.D. dissertation, Harvard University, United States—Massachusetts. Retrieved May 31, 2011, from Dissertations & Theses: Full Text.(Publication No. AAT 9910116).*

Rosenstein, Alan H., & Shulkin, David. (Sep. 1991). Changing Physician Behavior Is Tool to Reduce Health Care Costs. Health Care Strategic Management, 9(9), 14-6. Retrieved May 31, 2011, from ABI/Inform Global. (Document ID: 1103190).*

Office Action in co-pending U.S. Appl. No. 11/933,075 dated Dec. 21, 2010.

Office Action in co-pending U.S. Appl. No, 12/683,252 dated Dec. 15, 2010.

"Celadon Health Signs With Symmetry; Physician Incentive System Will Use Episode Treatment Groups (TM)", www.prnewswire.com, Phoenix, AZ.

Boyden, Andrew, Dr., et al., "The Appropriate Use of Financial Incentives to Encourage Preventive Care in General Practice", Centre for Health Program Evaluation, May 2000, Research Report 18, Australia.

Smith, David, "Think Twice Before Assuming Risk for Pharmacy Costs", Family Practice Management, 1999, http://www.aafp.org/fpm/990600fm/17.html.

Higgin, M., Securing the perimeter; Health Management Technology; Atlanta; Dec. 2000; vol. 21; Issue 12, pp. 8-12.

Landon, "A Conceptual Mode of the Effects of Health Care Organizations on the Quality of Medical Care," May 1998, JAMA, vol. 270, No. 17, pp. 1377-1382.

Rice, Physicians Payment Policies, 1997 Annual Review Public Health, pp. 549-565.

Glass, "Incentive-Based Physician Compensation Model," Jul. 1999, Journal of Ambulatory Care Management, pp. 36-40.

Segal, Influencing Physicians Prescribing, Oct. 1999, Pharmacy Practice Management Quarterly, pp. 30-50.

Cherney, Choosing as Advantageous Risk-Sharing Arrangement, Mar. 1999, Healthcare Financial Management, pp. 35-37.

Rosenstein, "Changing Physicians Behavior is Tool to Reduce Health Care Cost," Sep. 1991, Healthcare Strategic Management, vol. 9, Issue 9, pp. 14-16.

Snail, The Effects of Hospital Contracting for Physicians Services on Hospital Performance, Spring 2000, Univ. of California, Berkley, pp. 1-182.

Young, "Aligning Physican Financial Incentives in a Mixed-Payment Environment," Oct. 2000, Healthcare Financial Management, pp. 46-55.

Davis, "New Compensation Model Improves Physician Productivity," Jul. 1999, Healthcare Financial Management, pp. 46-49.

Shulkin, "Promoting Cost Effective Physician Behavior," Jul. 1993, Healthcare Financial Management, vol. 47, No. 7, pp. 48-54.

Schwartz, Creating a Benchmark Database, Jan.1998, Health Management Technology, pp. 65-66.

Office Action in co-pending U.S. Appl. No. 11/933,075 dated Sep. 27, 2011.

Securing the perimeter; Health Management Technology; Atlanta; Dec. 2000; Mark Higging; vol. 21; Issue: 12; Start pp. 8-12.*

Influencing Physician Prescribing; Richard Segal, PhD; 1999; pp. 1-21.*

Incentive-based Physician Compensation Models; Kathryn P. Glass, MBA, MSHA; 1999; pp. 1-10.*

Aligning physician financial incentives in a mixed-payment environment by David W. Young, Sheila M. McCarthy (Healthcare Financial Management; Westchester :Oct. 2000; vol. 54; Iss. 10; p. 46; pp. 1-10).*

Changing Physician Behavior Is Tool to Reduce Health Care Costs by Rosenstein, Alan H., Shulkin, David. Health Care Strategic Management. Chicago: Sep. 1991. vol. 9, Iss.9; p. 14, 3 pgs.*

Landon et al., A Conceptual Model of the Effects of Health Care Organizations on the Quality of Medical Care, May 1998, JAMA, vol. 270 No. 17, pp. 1377-1382.

Glass et al., Incentive-Based Physician Compensation Models, Jul. 1999, Journal of Ambulatory Care Management, pp. 36-46.

Segal et al., Influencing Physician Prescribing, Oct. 1999, Pharmacy Practice Management Quarterly, pp. 30-50.

Cherney, Choosing an Advantageous Risk-Sharing Arrangement, Mar. 1999, Healthcare Financial Management, pp. 35-37.

Rosenstein et al., Changing Physician Behavior is Tool to Reduce Health Care Costs, Sep. 1991, Healthcare Strategic Management, vol. 9, Iss. 9, pp. 14-16.

Snail, The Effects of Hospital Contracting for Physician Services on Hospital Performance, Spring 2000, University of California, Berkley, pp. 1-182.

Higging, M., Securing the perimeter; Health Managment Technology; Atlanta; Dec. 2000; vol. 21; Issue 12 Start pp. 8-12.

Landon et al., A conceptual Model of the Effects of Health Care Organizations on the Quality of Medical Care, May 1998, Jama, vol. 270, No. 17, pp. 1377-1382.

Rice, Physicians Payment Policies, 1997, Annual Review Public Health, pp. 549-565.

Glass et al., Incentive-Based Physician Compensation Models, Jul. 1999, Journal of Ambulatory Care Management, pp. 36-40.

Segal et al., Influencing Physicians Prescribing, Oct. 1999, Pharmacy Practice Management Quarterly, pp. 30-50.

Rosenstein et al., Changing Physicians Behavior is Tool to Reduce Health Care Costs, Sep. 1991, Healthcare Strategic Management, vol. 9, Iss. 9, pp. 14-16.

Young et al., Aligning Physician Financial Incentives In a Mixed-Payment Environment, Healthcare Financial Management, pp. 46-55 (Oct. 2000).

Davis et al., New Compensation Model Improves Physician Productivity, Jul. 1999, Healthcare Financial Management, pp. 46-49.

Schwartz, Creating a Benchmark Database, Jan. 1998, Health Management Technology, pp. 65-66.

File History of Lewis U.S. Appl. No. 09/812,704.

File HIstory of Lewis U.S. Appl. No. 11/933,075.

File History of Lewis U.S. Appl. No. 11/924,751.

* cited by examiner

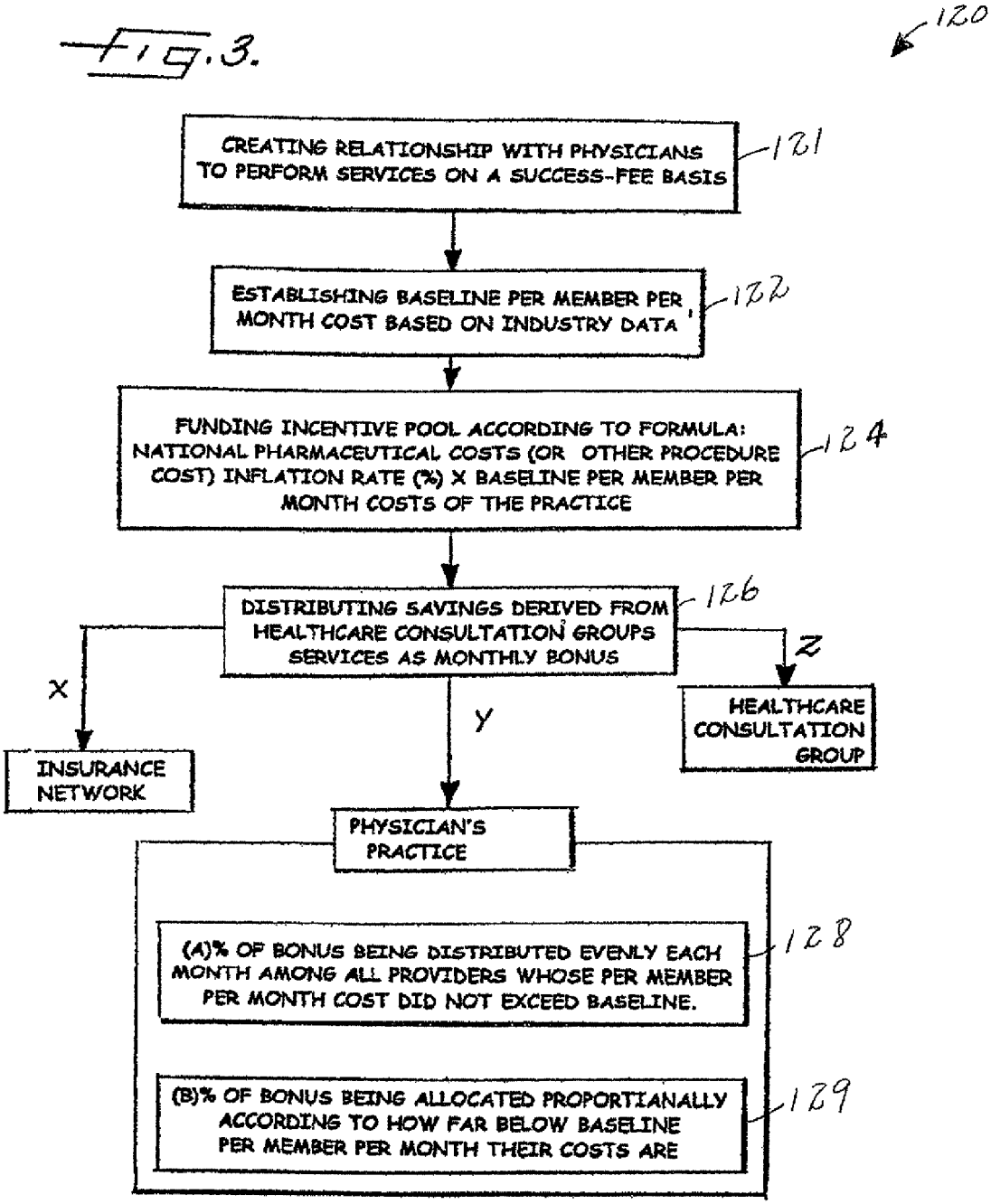
FIG. 3.
120
CREATING RELATIONSHIP WITH PHYSICIANS TO PERFORM SERVICES ON A SUCCESS-FEE BASIS
121
ESTABLISHING BASELINE PER MEMBER PER MONTH COST BASED ON INDUSTRY DATA
122
FUNDING INCENTIVE POOL ACCORDING TO FORMULA: NATIONAL PHARMACEUTICAL COSTS (OR OTHER PROCEDURE COST) INFLATION RATE (%) X BASELINE PER MEMBER PER MONTH COSTS OF THE PRACTICE
124
DISTRIBUTING SAVINGS DERIVED FROM HEALTHCARE CONSULTATION GROUPS SERVICES AS MONTHLY BONUS
126
X
Y
Z
INSURANCE NETWORK
HEALTHCARE CONSULTATION GROUP
PHYSICIAN'S PRACTICE
(A)% OF BONUS BEING DISTRIBUTED EVENLY EACH MONTH AMONG ALL PROVIDERS WHOSE PER MEMBER PER MONTH COST DID NOT EXCEED BASELINE.
128
(B)% OF BONUS BEING ALLOCATED PROPORTIANALLY ACCORDING TO HOW FAR BELOW BASELINE PER MEMBER PER MONTH THEIR COSTS ARE
129

Current prescription
New prescription
Advantages
48
48
27
40
PHARMACY
INSURANCE CLAIMS DATABASE
COMMUNICATION NETWORK
100
FEEDBACK TO PHYSICIAN'S OFFICES
PHARMACY BENEFITS MANAGER
20
108

U
PATIENT CHART, INSERT

METHODS FOR COLLECTING FEES FOR HEALTHCARE MANAGEMENT GROUP

Matter enclosed in heavy brackets [ ] appears in the original patent but forms no part of this reissue specification; matter printed in italics indicates the additions made by reissue.

RELATED APPLICATIONS

The application is related to U.S. patent application Ser. No. 09/812,704, now U.S. Pat. No. 7,398,217, titled "Methods and Systems For Healthcare Practice Management" filed on the same date herewith by the same inventors, which is incorporated herein by reference in its entirety.

FIELD OF THE INVENTION

The present invention relates to the healthcare industry and, more particularly, to the field of healthcare management.

BACKGROUND OF THE INVENTION

In the healthcare industry, as illustrated in FIG. 1, physicians generally organize themselves into practice groups 25 and normally subcontract to an insurance network 30. The insurance network 30 is not limited to traditional insurance networks, i.e., Blue Cross Blue Shield, Aetna, United Healthcare, etc., but also includes [self insured] *self-insured* networks within companies, employers, or other large entities. The insurance network 30 includes a plurality of patients 35 that obtain healthcare services from the plurality of physicians 25 participating in the insurance network 30. The groups of physicians 25 include a plurality of physicians 25 that provide healthcare services to a plurality of patients 35 within a particular geographical area in varying medical fields. The physicians in the healthcare practices 25 are normally compensated a predetermined reimbursement amount by the insurance network 30 for every subscribing patient 35 in the insurance network 30 that is to be treated by the physicians 25.

For example, a physician 25 participating in the insurance network 30 may be reimbursed $80 per month by the insurance network 30 for agreeing to treat a patient 35 in the insurance network 30 and assuming the responsibility for a percentage of the ancillary medical costs for that patient 25. As illustrated in FIG. 1, there exists a relationship between the insurance network 30 and the physician practice 25. Likewise, there also [exjsts] *exists* a relationship between the patients 35 and the insurance network 30, and the patients 35 and the physician practices 25. The physician practice 25 normally receives payment for services directly from the patients 35 or though reimbursements from the insurance network 30. The payment that is received from the patient 35 can be in the form of a co-payment or a partial payment for the [healiheare] *healthcare* services. In order for the physician practice 25 participating in the insurance network 30 to receive the entire reimbursement from the insurance network 30, i.e., the $80 per month for agreeing to treat each patient 35, the physician practice 25 must comply with preselected requirements set by the insurance network 30. These requirements often fall within varying cost centers, such as pharmaceutical, laboratory, anesthesiology, and radiation costs, for example.

In the pharmaceutical area, for example, a wide variety of prescription medications are developed and manufactured to combat similar illnesses. As illustrated in FIG. 1, prescription medication manufacturers 24 sometimes enter into agreements with the insurance network 30. The prescription medication manufacturers 24 sometimes offer rebates to insurance networks 30 if the physician practice 25 prescribes their medications. The prescription medication manufacturers 24 cannot enter into these types of agreements with the physician practices 25, as it would likely be contrary to public policy. The insurance network 30, in turn may enter into an agreement with a pharmacy network 21, such as a pharmacy benefits management (PBM), for example, to encourage the physician practice 25 in the insurance network 30 to prescribe certain medications. The PBM is compensated a profit on the preferred prescription medications, and a portion of the profits are then passed along to the pharmacy 40. The requirements, or preferences, set by the insurance network 30 regarding pharmaceutical costs, for example, include the types of prescription medications that the physicians may prescribe to their patients.

In some instances, the insurance networks provide incentives to the physician practice 25 for prescribing medications upon which, the insurance network 30 receives discounts from prescription medication manufacturers 24. If the physician practice 25 bears any percentage of medication costs for the patient 35 and prescribes medications which differ from those preferred by the insurance network 30, the incentives may be withheld from the physician practice 25, i.e., the physician practice 25 may be paid nothing instead of $10 for the patient 35 in the insurance network 30. As illustrated in FIG. 1, the insurance network 30 monitors the prescriptions that the physician practice 25 participating in the insurance network 30 writes through a monitoring relationship developed with pharmacies 40 and pharmacy networks 21. In this monitoring relationship, the pharmacy 40 and the PBM provide claims data to the insurance network 30.

There are many different levels of risk for the physician practice 25 that is associated with this arrangement. If the insurance network 30 assumes the financial responsibility for the patient's 35 healthcare needs, then the physician practice 25 assumes no risk. If, however, the physician practice 25 assumes the financial responsibility for the patient's healthcare needs, i.e., any healthcare costs beyond the reimbursement amount from the insurance network 30, then the physician practice 25 assumes the most risk. Another alternative arrangement is if the financial responsibility for the patient's 35 healthcare needs are shared between the physician practice 25 and the insurance network 30. In such an arrangement, the risk for patient's 35 healthcare costs is shared between the insurance network 30 and the physician practice 25. As illustrated in FIG. 1, the payments between the insurance network 30 and the physician practice 25 can vary depending upon the amount of risk taken by the physician practice 25.

As further illustrated in FIG. 1, patients 35 participating in the insurance network 30 obtain healthcare treatment from the physician practice 25 and pay premiums or insurance payments to the insurance network 30. The medical treatment provided to the patients 35 by the physicians in the physician practice 25 can include prescribing medications. The patients 35, however, obtain the prescription medications from the pharmacy 40 and provide either a full payment or a co-payment for the prescription medications. The patients 35 can then be reimbursed for some or all of the payment for the prescription medications from the insurance network 30.

This arrangement is disadvantageous for the physician practice 25 participating in the insurance network 30 because it requires a great deal of management and organization to follow the requirements of the insurance network 30. The system is even more disadvantageous for the physician practice 25 if it participates in multiple insurance networks 30. Each insurance network 30 maintains a preferred list of prescription medications, for example, that the physician practice 25 may prescribe to the patients 35. Further, each insurance network 30 updates their preferred list of prescription medications on a routine basis. The physician practice 25 in the insurance network 30 generally attempts to spend the majority of their time treating patients 35. The management and organization of the insurance network 30 requirements can be time consuming and eliminate some of the time that a physician practice 25 may normally dedicate to the treatment of patients 35.

Traditionally, there also has been tension between the physician practice 25 and the insurance network 30. The tension can be caused by the insurance network 30 delaying payment to the physician practice 25 with notification of a particular network requirement that has been violated, if any. In addition, the physician practice 25 normally receives very little support from the insurance network 30, such as patient history updates and information on medication costs. Tensions are also sometimes caused by the insurance network's 30 perception that the physician practice 25 over-bills for treatment and does not provide all possible treatment options for patients 35. The physician practice 25 sometimes feel pressured by the insurance network 30 to provide medical treatment to their patients 35 according to the preferences of the insurance network 30 instead of according to their own medical judgments. Of course, the physician practice 25 is free to independently treat the patients 35 in the insurance network 30 based on medical judgment, but the tension between the physician practice 25 and the insurance network 30 still exists.

The physician practice 25 is not bound by the treatment procedures that are preferred by the insurance network 30. Often, however, conflict between the insurance network 30 and the physician practice 25 can arise when the insurance network 30 prefers the physician practice 25 to perform certain medical procedures or prescribe particular medications that are more profitable to the insurance network 30. The physician practice 25 does not have the time necessary to perform exhaustive research necessary to determine if the treatment proposed by the insurance network 30 is feasible, or even safe, to patients 35. Prudent physicians in the physician practice 25 often do not change their treatment practices based simply on information provided by the insurance networks 30.

In the interest of patient safety, physicians in the physician practice 25 should research medical literature to become more educated as to possible benefits of alternative medications. As noted above, however, this takes a great deal of time that can better be used to treat patients 35. In order to conserve the time that might normally be spent on managing and organizing the insurance network 30 requirements, however, some physician practices 35 may hire office managers. This is disadvantageous because an office manager can be extremely costly and will normally need office space. The office space that may be used by the proposed office manager may be an examination room in which the physician would normally treat patients 35. Once again, this cuts down on the number of patients 35 that the physician practice 25 can possibly treat. The office manager also often only manages finances and personnel and has little understanding of physician practices 25 with respect to relationships between insurance networks 30 and physicians' 25 decisions and practices with respect to patients 30.

It has been proposed that the performance of a first healthcare provider can be compared to the performance of a second healthcare provider using a computer program as described in U.S. Pat. No. 5,652,842 titled "Analysis and Reporting of Performance of Service Providers", by Siegrist, Jr. et al. More particularly, a method of monitoring customer satisfaction so as to keep the healthcare providers competitive in many different fields is described. The method described in Siegrist, Jr. et al., however, is disadvantageous to group physicians in organizing and managing healthcare costs that are dependant upon preferred treatment of the insurance network.

Often times, in an effort to become more profitable, a healthcare practice 25 or a self insured employer may study the current relationship between the healthcare practice group 25 and the insurance network 30 or hire a business consultant to analyze this relationship and make recommendations as to how to become more profitable. This, however, is disadvantageous because the business consultant does not have accountability for the results. In other words, the business consultant analyzes the situation, makes a recommendation, and collects a fee for the time spent in analyzing the situation. This is normally the end of the relationship between the business consultant and the physician 25. The responsibility for implementation is then shifted to the healthcare practice 25, with some added knowledge provided by the business consultant who has collected a fee and exited the situation, to make the practice more profitable with no assistance.

Hiring a business consultant is also disadvantageous because the healthcare practice 25 has to assume risk for engaging the business consultant to review the healthcare practice 25. This is also disadvantageous because prudent physicians will normally take time to evaluate the expertise of the business consultant if the situation calls for the healthcare practice 25 to assume a risk. This is further disadvantageous because the healthcare practice 25 is left with the responsibility of implementing the suggestions of the business consultant in cases where the consultant merely analyzes the situation and provides information.

When the physician practice 25 is not able to organize and manage medical treatment information in a manner that is preferred by the insurance network 30 in which they participate, there only exist two possible results. Either the physician practice 25 receives lower reimbursements from the insurance network 30, or the insurance network 30 is less profitable. No matter which result occurs, however, the ultimate end result is higher medical costs for patients 35. Therefore, the patients 35 are the real losers in the situations described above.

SUMMARY OF THE INVENTION

With the foregoing in mind, the present invention advantageously provides a system and methods for optimizing profits of a healthcare practice. The system and methods of the present invention also advantageously assist physicians and insurance providers in providing cost-effective healthcare services to patients. The present invention additionally advantageously eliminates the time necessary for physicians to conduct exhaustive research in determining if alternative, and more profitable, ancillary medical procedures are beneficial to their patients. The present invention also advantageously substantially reduces manpower, expense, and tool-development necessary to implement management changes that decrease healthcare costs. The system and methods of the present invention further advantageously assist in controlling the rising costs of medical care by reducing physicians' ancillary medical costs. The present invention still further advantageously strengthens the relationship between physicians and insurance providers by providing an intermediary between the two. The present invention also advantageously decreases financial risk for a healthcare practices or an insurance network in engaging a healthcare consultation group to manage healthcare costs.

The present invention also advantageously provides a pricing, billing, or charging structure that provides accountability to a healthcare consultation group. If the healthcare consultation group can be held accountable for performance, then healthcare practices and insurance networks are more likely to trust it. Further, the healthcare practice and the insurance network are provided an incentive to employ the services of the healthcare consultation group.

More particularly, the present invention provides a method of collecting fees for managing and optimizing the profitability of a plurality of physicians in a healthcare practice participating in an insurance network. The method includes the step of establishing a relationship between a healthcare consultation group and the healthcare practice participating in the insurance network to increase the physician's profitability by reducing a risk of not receiving a predetermined reimbursement amount for ancillary medical costs from the insurance network. The method also includes the step of distributing predetermined percentages of savings attributed to the physicians' modified ancillary medical cost management behavior. The method of collecting fees can also advantageously include the step of funding an incentive pool to be paid to the healthcare practice participating in the insurance network if the healthcare costs of the plurality of physicians in the healthcare practice decrease to a predetermined level over a preselected period of time.

The present invention also advantageously includes a method of collecting fees for managing and optimizing the profitability of an insurance network having a plurality of physicians in a healthcare practice participating therein. The method advantageously includes the step of establishing a relationship between a healthcare management consultation group and the healthcare practice participating in the insurance network to increase the insurance network's profitability by limiting the plurality of physicians' ancillary medical cost management behavior that is not preferred by the insurance network. The method also includes the step of distributing predetermined percentages of savings attributed to the physicians' modified ancillary medical cost management behavior.

The present invention advantageously includes the formation of a team relationship working towards a common goal having aligned incentives, i.e., a team working towards the goal of enhancing profitability. The present invention also advantageously provides accountability to the healthcare consultation group. Accountability will ease the minds of the healthcare practice and insurance network giving the healthcare consultation group a chance to prove that profits can be enhanced. This arrangement advantageously allows all involved to gain, including patients, through more cost-effective medical care. The present invention also advantageously eliminates the time necessary for healthcare practices and insurance networks to research references of the healthcare consultation group because there is no risk for the insurance network or the healthcare practice to engage the healthcare consultation group.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 3 is a flow chart describing the method of managing ancillary medical costs and optimizing profitability for an insurance network according to the present invention;

DETAILED DESCRIPTION OF PREFERRED EMBODIMENTS

The present invention will now be described more fully hereinafter with reference to the accompanying drawings which illustrate preferred embodiments of the invention. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, the prime notation, if used, indicates similar elements in alternative embodiments.

Figure 1:
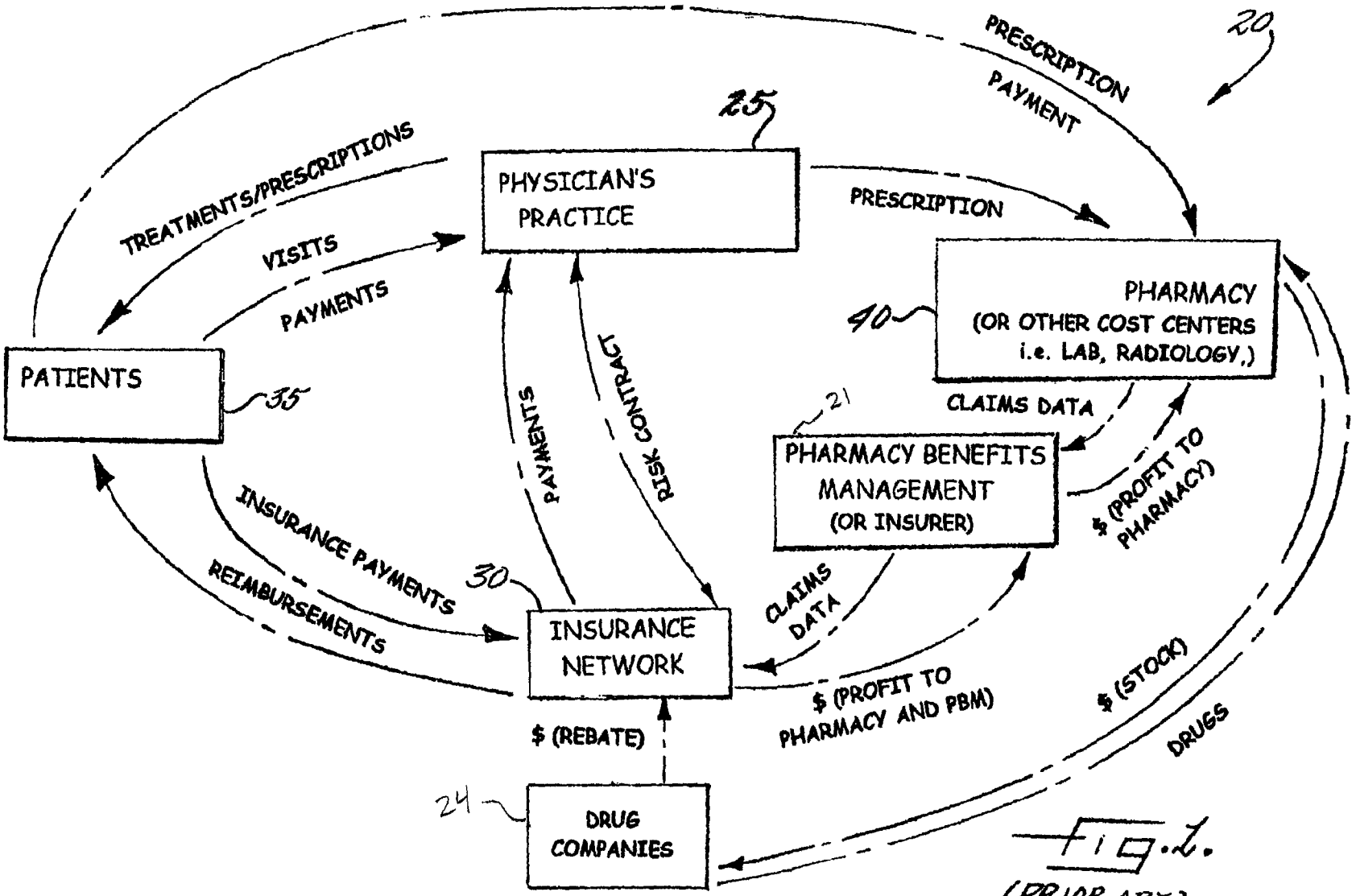
FIG. 1. (PRIOR ART)
FIG. 1 is a schematic view of a typical relationship between physicians, insurance networks, and patients according to the prior art.
Figure 1A:
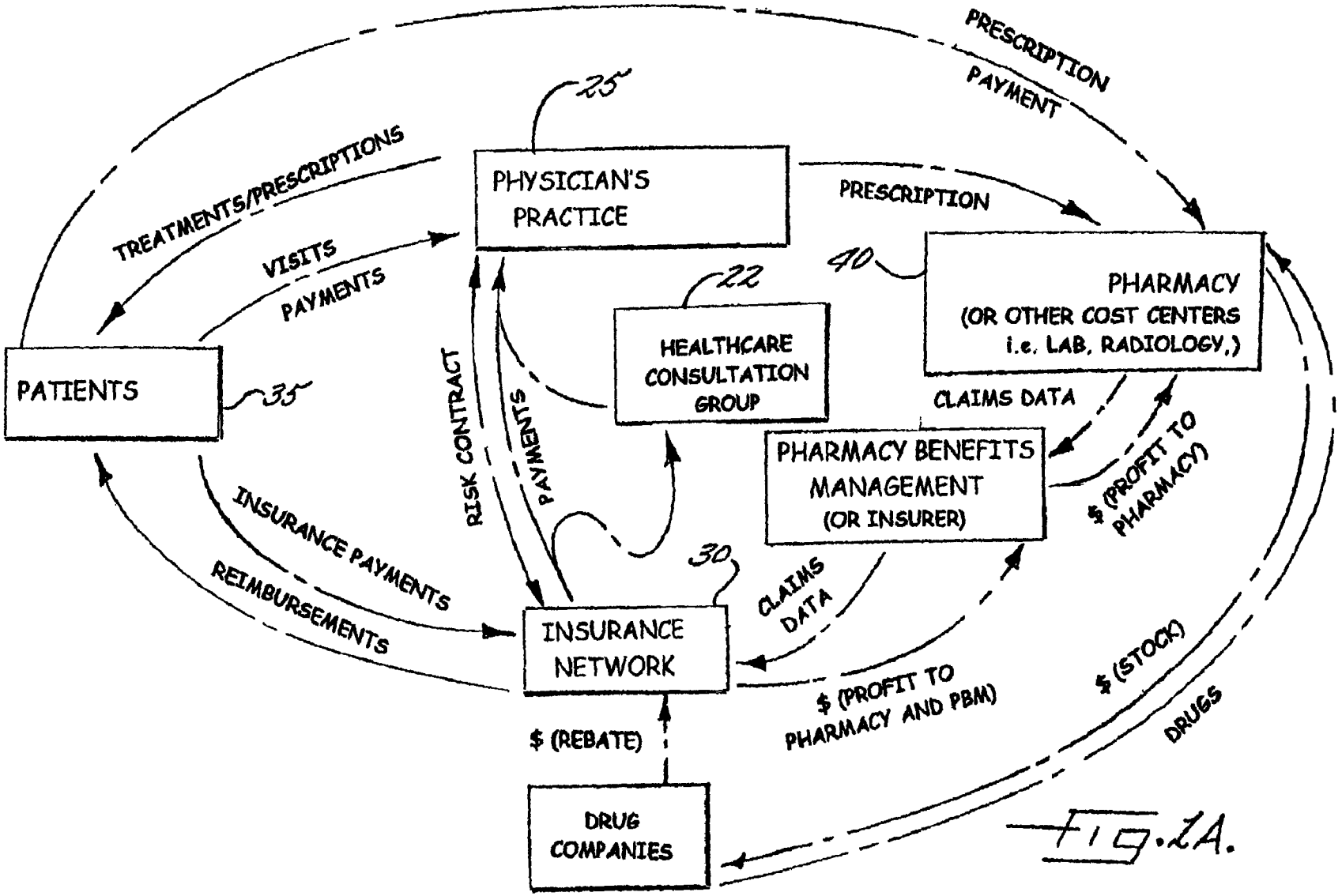
FIG. 1A is a schematic view of a relationship between physicians, insurance networks, patients, and a healthcare consultation group according to the present invention.

FIGS. 1A-6A illustrate systems and methods of optimizing profitability of healthcare practices and insurance networks by managing ancillary medical costs. As illustrated in FIG. 1A, the present invention preferably includes a healthcare consultation group 22 that forms an intermediary relationship between a healthcare practice 25 and an insurance network 30. The healthcare practice 25 preferably includes a plurality of physicians 27 practicing in one or more medical fields in a particular geographic area. The healthcare consultation group 22 determines the most efficient manner to manage ancillary medical costs to thereby increase profitability of the healthcare practice 25 and the insurance network 30 by decreasing ancillary medical costs. In cases where the financial responsibility for patient care is divided between the insurance network 30 and the healthcare practice 25, the healthcare consultation group 22 can also advantageously manage ancillary medical costs of the insurance network 30 and the healthcare practice 25 to thereby decrease ancillary medical costs, thereby increasing profitability of both the insurance network 30 and the healthcare practice 25. Ancillary medical costs can include pharmacy costs, for example. The ancillary medical costs can also advantageously include any one of a number of medical cost centers such as taken from federally-defined hospital departments. These can include, but are not limited to, anesthesiology, blood, blood storage procedure and administration, radiology, electroencephalogram (LEG), electrocardiogram (EKG), emergency room, IV therapy, organ and tissue acquisition, labor and delivery, medical/surgical supplies, nuclear medicine, occupational therapy, operating room, physical therapy, recovery room, renal dialysis, respiratory therapy, special care, speech therapy, and therapeutic radiology. These general categories also can be broken down into more specific categories as understood by those skilled in the art.

As perhaps best illustrated in FIGS. 1A-4, the present invention provides methods for managing a healthcare practice 25 to optimize the profitability of the healthcare practice 25 by decreasing the healthcare costs of the healthcare practice 25. As illustrated in FIG. 3, the present invention also provides methods of optimizing the profitability of an insurance network 30 having a plurality of physicians 27 in a healthcare practice 25 participating therein by managing ancillary medical costs i.e., pharmacy costs, of the healthcare practice 25, or a combination of the healthcare practice 25 and the insurance network 30. The present invention is particularly advantageous for use in association with pharmacy cost because of the large year to year increases in the cost of prescription medications and other pharmaceutical related costs. The method of managing the healthcare practice 25 and the method of optimizing the profitability of the insurance network 30 includes gathering data 50 from each of the plurality of physicians 27 in the healthcare practice 25 participating in the insurance network 30 regarding management of ancillary medical costs. The step of gathering data 50 preferably includes conferring with the healthcare practice 25 and the insurance network 30 to determine 53 the number of patients 35 participating in the insurance network 30 and the current ancillary medical procedure used to treat those patients 35. In a case where the ancillary medical cost is pharmacy cost, for example, the method includes gathering data from the physicians 27 regarding the number of pharmacy claims over a predetermined period of time, the number of patients 35 treated by the physician 27, and demographic information about the physician 27.

Data is also gathered 52 from ancillary medical facilities 40 regarding ancillary medical costs of each of the plurality of physicians 27 in the healthcare practice 25 participating in the insurance network 30. This data can advantageously include claims information, claim types, and cost data regarding the claims. This data can also advantageously be gathered from the healthcare practice 25 or the insurance network 30. The data collected from the ancillary medical facilities 40 can be available on an ancillary medical network database, such as a pharmacy network listing pharmacy costs for each of a plurality of physicians 27 in the healthcare practice 25. Again, in a case where the ancillary medical cost is pharmacy cost, for example, the method of gathering data 50 includes obtaining average wholesale pharmacy costs from pharmacy networks such as First Databank, Red Book, and Blue Book, for example, or any other pharmacy network as understood by those skilled in the art. The step of gathering data 50 from the pharmacy also includes getting monthly updates from the pharmacy network regarding average wholesale pharmacy costs. The step of gathering data 50 further preferably includes extrapolating a contracted price of prescription medications from the pharmacy claims data.

If the ancillary medical cost is pharmacy cost, for example, then the step of gathering data 50 can advantageously include preparing a management report that includes information regarding the physician's pharmacy cost performance measured by per member per month (PMPM) costs. The management report can also advantageously include a physician report card to inform the physician 27 of current performance and high cost patient reports from the physician 27. The report card is advantageously detailed for each physician 27 based on prescribing patterns, costs of management behavior to them and the healthcare practice 25, peer-reviewed alternative prescription medications, and potential savings if followed. The report cards are then presented to the identified physician 27 so that they can perform their own analysis. The healthcare practice 25 can advantageously encourage the physician 27 to give the report consideration. The management report can also advantageously include a list of the top medication providers, e.g., the top fifty high-cost prescription medication providers and a pharmacy cost management report.

The method of managing the healthcare practice 25 and the method of optimizing the profitability of an insurance network both further preferably include identifying 56 at least one physician 27 in the healthcare practice 25 that is engaging in ancillary medical procedures that are not as profitable or preferred by the insurance network 30. Physicians 27 who engage in the ancillary medical procedures that are not preferred by the insurance network 30 are sometimes at risk of not receiving a predetermined reimbursement amount from the insurance network 30. These ancillary medical procedures can include the prescription of medications that are not as profitable to the insurance network 30 or the physicians 27 in the healthcare practice 25. In cases where the financial responsibility for patient 35 care is shared between the healthcare practice 25 and the insurance network 30, then the profitability of both the insurance network 30, and the healthcare practice 25 are enhanced. Typically, alternative medications are available that combat the same illnesses. In some instances, however, either the physician is not familiar with the alternative medication or the patient 35 insists on a particular brand-name medication merely because the brand-name medication has been greatly advertised, marketed, or commercialized.

The step of identifying the at least one physician 56 preferably includes analyzing the data 58 collected from the physicians and the ancillary medical network databases to determine the ancillary medical costs of each physician 27 in the healthcare practice 25. The step of identifying the at least one physician 56 also preferably includes calculating 60 an average ancillary medical cost per physician in the healthcare practice 25. After an average is calculated 60, physicians 27 having ancillary medical costs that fall a predetermined standard deviation away from the average, e.g., two standard deviations from the average of their peers in the healthcare practice 25, are identified 56 and targeted for intervention. Should a point be reached where no physician 27 falls beyond the two standard deviation limit, then a predetermined percentage of the physicians having the highest or higher than average ancillary medical costs will be considered for intervention.

The method of managing the healthcare practice group 20 and optimizing the profitability of an insurance network 30 both further include identifying patients 35 and ancillary medical procedures that have costs above the average ancillary medical cost calculated above. For example, the step of identifying patients 35 whose ancillary medical costs are greater than the average ancillary medical costs per physician 27 can include identifying patients 35 who have pharmacy costs greater than the average pharmacy cost of the physician 27. Another example preferably includes identifying prescription medications having a higher cost than the average prescription medication cost of the healthcare practice 25.

When the physician 27 that has ancillary medical costs greater than the average ancillary medical costs of the healthcare practice 25 is identified, the method of managing the healthcare practice group 20 and optimizing the profitability of an insurance network 30 both further include conferencing with the identified physician 27 to discuss the impact of not taking any action regarding ancillary medical cost overruns.

The method of managing the [healtheare] *healthcare* practice 20 and the method of optimizing the profitability of an insurance network 30 both further include modifying the physician's management behavior 65 regarding the ancillary medical costs. The physician's management behavior is modified to advantageously reduce the risk of not collecting the predetermined reimbursement amount from the insurance network 30 to thereby increase the physician's profitability. The physician's modified management behavior can also advantageously increase the profitability of the insurance network 30.

The step of modifying the physician's management behavior includes educating 70 the at least one physician 27 on benefits of alternative ancillary medical procedures. The education 70 of the physician 27 can be performed using research literature for comparing the alternative ancillary medical procedures to current ancillary medical procedures. The education 70 can further include organizing continued medical education classes 71 through ancillary medical facilities and can also include the education 72 of nurses and ancillary staff members. This is advantageous because continued medical education classes are generally required in order for a physician 27 to keep licensing requirements current. The continued medical education can advantageously fulfill the physician's licensing requirement while simultaneously educating the physician 27 as to the benefits of alternative ancillary medical procedures that may be more advantageous to themselves as well as to their patients.

The step of educating 70 the at least one physician advantageously includes providing the at least one physician national treatment guidelines for stepwise treatment of disease states. Too often prescription medication representatives, such as sales representatives, convince physicians 27 that the newest medication is necessary to treat patients 35 and other regimens should be skipped or abandoned. The step of educating 70 the physicians 27, therefore, includes recommending that physicians 27 follow nationally recognized guidelines and treatment protocols, such as from the Center for Disease Control (CDC) and the National Institute of Health (NIH), for example.

This advantageously ensures that community accepted standards of care are being provided. The step of educating 70 the physicians 27 also advantageously includes identifying the medications of choice for given disease states and verifying, through data analysis and dialog, that medical research indicates that modified physicians behavior will have a favorable impact. The step of educating 70 the physicians 27 using peer-reviewed, medical research based literature recommending nationally recognized guidelines also advantageously decreases liability incurred by physicians 27. The physicians' 27 medical malpractice liability can advantageously be decreased if the physician follows nationally recognized guidelines and treatment protocols.

The step of modifying the physician's management behavior also includes providing patient history updates. If, for example, the physician 27 makes a decision to modify a patient's 35 prescription medication in the interest of decreasing pharmacy cost, for example, the patient history updates become very advantageous for the general safety and welfare of the patient 27. At the time of ordering the new prescription, physicians 27 may not have all the patient's 35 medical history to prescribe a medication without inducing an adverse drug reaction (ADR). ADR's often lead to increased repeat visits to the physician 27 for the same ailment and possibly to a hospital, which increase the healthcare practice's 25 health care cost tremendously. After the gathered data, provided by a pharmacy benefits management (PBM) company or a pharmacy claims benefit administrator, for example, is analyzed, printouts of the patients' 35 prescription history can advantageously be provided to the physician 27. These printouts may be included in patient 35 charts for up-to-date reference by the physicians 27.

Figure 2A:
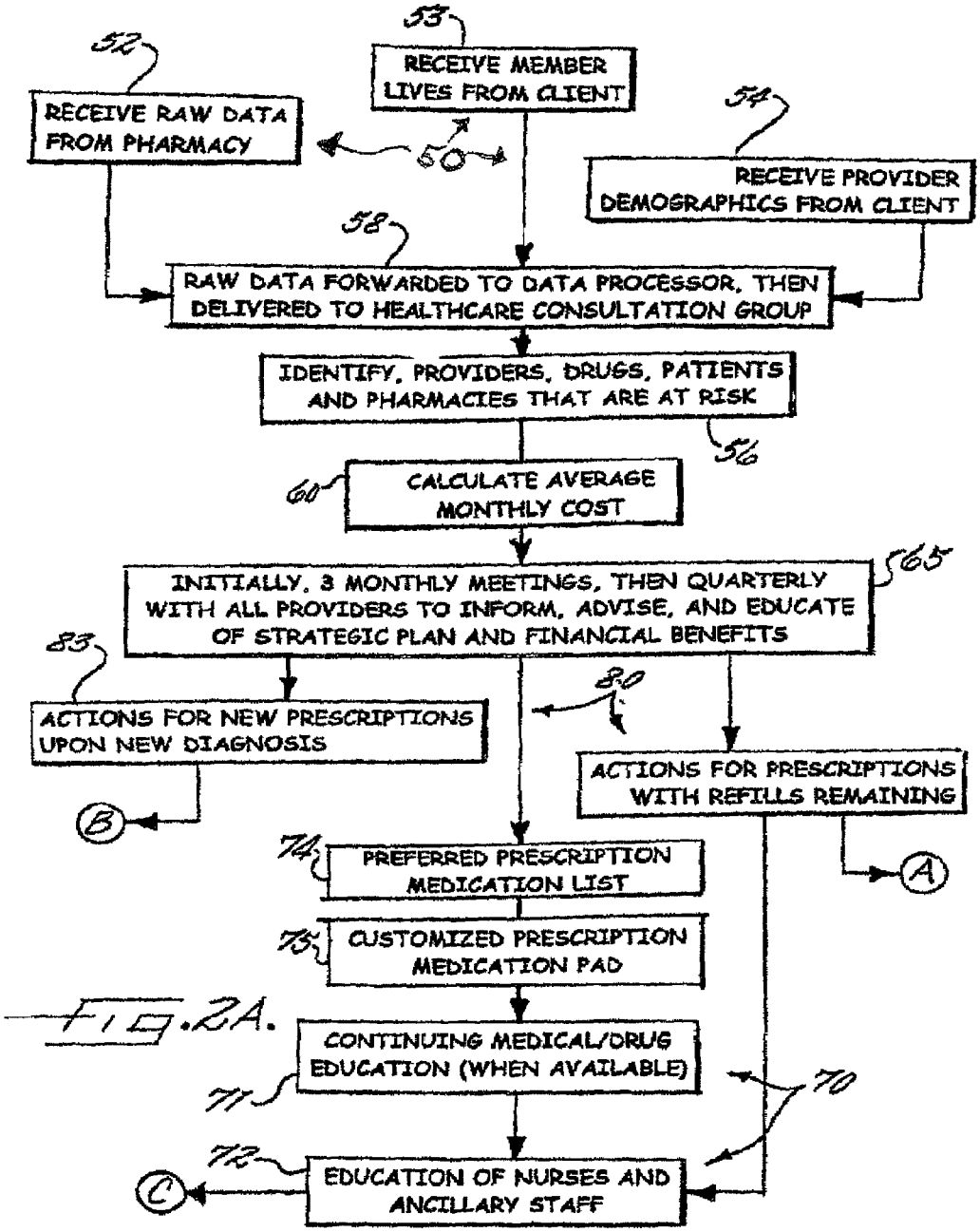
FIG. 2A is a flow chart describing the method of managing ancillary medical costs for healthcare practices and insurance networks according to the present invention.

As best illustrated in FIG. 2A, the method of managing the healthcare practice 25 and the method of optimizing profitability of the insurance network 30 further includes providing a list of ancillary medical procedures, e.g., a list of preferred prescription medications, that are preferred by the insurance network 30. If the physicians 27 follow the suggested ancillary medical procedure list, the physicians 27 are more likely to receive the predetermined reimbursement from the insurance network 30, thereby providing enhanced profits to the physicians 27 as well as to the insurance networks 30. The enhanced profitability advantageously allows the insurance network 30 and the physicians 27 to provide more cost-effective medical treatment to the patients.

As also illustrated in FIG. 2A, the methods of managing the healthcare practice 25 and optimizing profitability of the insurance network 30 also advantageously include providing custom ancillary medication procedure forms 75, i.e., custom prescription medication pads, for use by the physician 27 to easily recognize which ancillary medical procedures are preferred by the insurance network 30. For example, the physician 27 is provided a custom prescription medication pad 75 that includes a vast list of prescription medications that are preferred by the insurance network 30. This eliminates the time necessary for the physician 27 to perform research on which medications are preferred by the insurance network 30.

Physicians 27 sometimes participate in a number of insurance networks 30. Differing insurance networks 30 normally have differing preferred ancillary medical procedures. When the physicians 27 participate in differing insurance networks 30, it becomes difficult to determine which ancillary medical procedures are preferred by each of the different insurance networks 30. The various insurance networks 30 normally have overlapping ancillary medical procedures. Therefore, the step of providing custom ancillary medical procedure customization forms also includes the step of providing custom ancillary medical procedure forms that account for the overlapping ancillary medical procedures of the various networks and advantageously eliminate the need for the physician 27 to take the time to research what insurance network 30 the patient 35 participates in and which ancillary medical procedures are preferred by the particular insurance network 30 in which the patient 35 participates. The custom ancillary medical form that accounts for overlapping ancillary medical procedures between various insurance networks 30 advantageously allows the physician 27 to engage in any ancillary medical procedure that is listed on the form without any risk of not receiving the predetermined reimbursement amount from the insurance network 30.

Figure 2B:
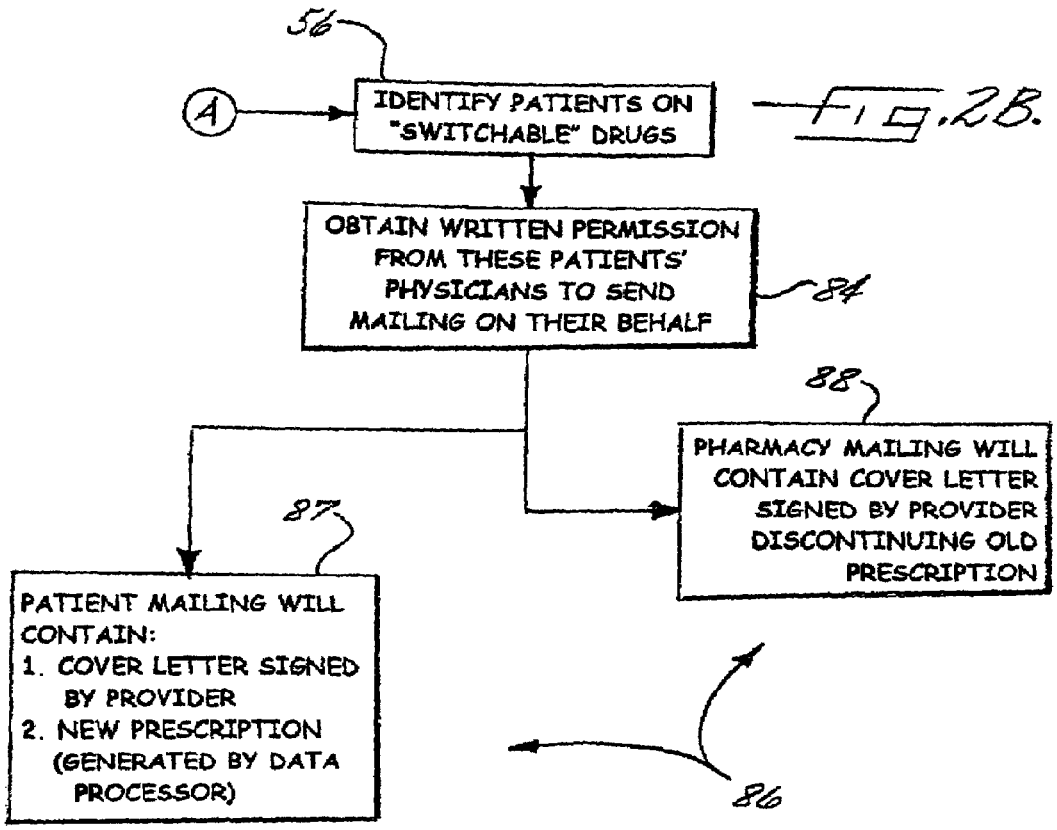
FIG. 2B is a flow chart describing the method of modifying ancillary medical procedures according to the present invention.
Figure 2C:
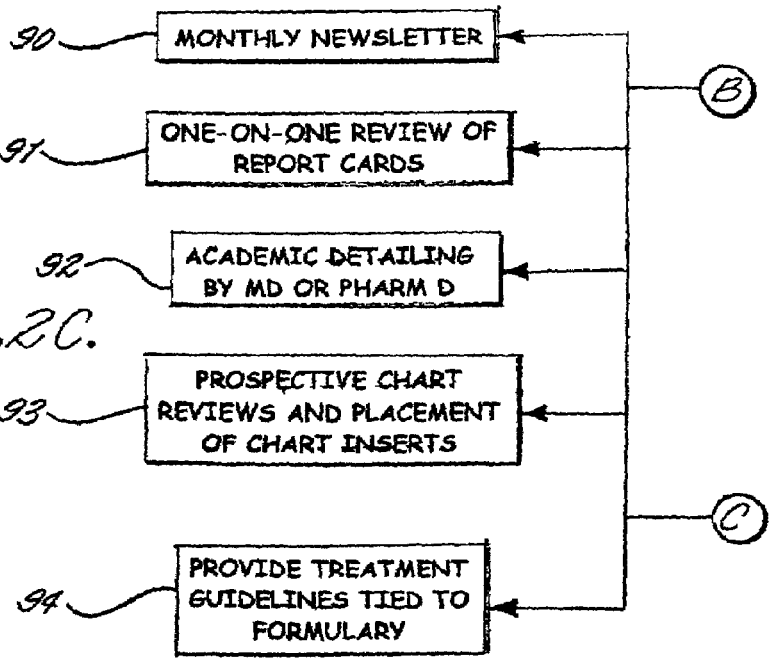
FIG. 2C is a flow chart describing the method of educating physicians on the benefits of alternative ancillary medical procedures according to the present invention.

As best illustrated in FIG. 2A-2C the methods of managing a healthcare practice 25 and optimizing profitability of an insurance network 30 of the present invention also include providing patient intervention 80 to enhance the profitability of the physicians 27 and the insurance networks 30. One source of increased ancillary medical costs are unnecessary patient requests. The patients 35 sometimes request particular ancillary medical procedures because of a lack of knowledge regarding alternative ancillary medical procedures. For example, some patients 35 insist on brand-name medications that are largely commercialized without having the requisite knowledge to make an informed decision regarding alternative ancillary medications. The step of providing patient intervention 80 advantageously includes identifying 56 the patients who participate in ancillary medical procedures that are not preferred by the insurance network 30 and put the physician 27 at risk of not receiving a predetermined reimbursement from the insurance network 30. The method of providing the patient intervention 80 also advantageously includes discontinuing the current ancillary medical procedure and amending it with a new ancillary medical procedure that is preferred by the insurance network 30 and reduces the risk of the physician 27 not receiving the predetermined reimbursement amount from the insurance network 30.

The step of providing patient intervention can advantageously include contacting patients 35 that are affected by poly-pharmacy and non-compliance, for example. The step of contacting patients includes contacting the patients 35 on a monthly basis. Poly-pharmacy occurs when the patient 35 is taking medications with ADR's, unnecessary medications, or those from the same medication class. In addition, if it is discovered during the step of analyzing the gathered data that the patient 35 is not taking the prescription medication as required, the step further includes contacting the patient 35 with a directive to comply with the treatment protocols. The contact to the patient 35 can, for example, be made in the form of a letter written on the physician's 27 letterhead.

The step of providing patient intervention also advantageously includes determining if stronger disease state management techniques are required. This determination is conducted on a monthly basis. For those patients 35 with aggressive diseases, specialist organizations are employed to provide recommendations to the physicians 27 and the patients 35 on the latest treatments techniques.

The steps of discontinuing and amending current ancillary medical procedures include providing information to the patients 35 regarding the benefits of the new alternative medical procedure, e.g., information that a lay-patient can understand regarding the benefits of an alternative prescription medication. The step of providing patient intervention also includes providing a monthly review of patient's charts to determine if the new ancillary medical procedures are sufficient for the patient's treatment. As patients are identified 56 that are not being treated per guidelines of alternative ancillary medical procedures, a chart 48 is advantageously inserted into a patient's medical chart, recommending an alternative ancillary medical procedure. The chart insert 48 advantageously includes an explanation of the recommended and pre-written ancillary medical procedure orders, i.e., pre-written prescriptions, for the physician's approval.

The physicians 27, however, do not always yield to the preferred ancillary medical procedures of the insurance network 30. When the physicians 27 encounter a situation where, relying on their vast medical knowledge, they know a proposed ancillary medical procedure is detrimental to the patient 35, then the insurance network 30 is approached to consider modifying their preferred ancillary medical procedures. Like the physicians 27, the insurance network 30 is educated regarding the benefits of the ancillary medical procedure that they seek to modify. This advantageously levels the playing field between physicians 27 and insurance networks 30. The present invention provides for the possibility that the insurance network 30 will yield to the medical judgment of the physician 27 concerning the treatment of patients 35.

The step of discontinuing an ancillary medical procedure further includes the step of preparing a plurality of letters 86. The step of preparing letters includes the healthcare consultation group 22 obtaining permission 84 from the physician 27 to distribute letters 87 to the patients 35 that are candidates for modification of ancillary medical procedures. One of the plurality of letters informs the ancillary medical facility of the discontinuation of a particular ancillary medical procedure 88. Another of the plurality of letters informs the patient that a particular ancillary medical procedure is discontinued 87. The letters can advantageously be written on the physician's letterhead. The letter to be sent to the patient 35 advantageously includes a detailed explanation of why the ancillary medical procedure is being modified, the benefits of the new ancillary medical procedure, and the advantages that patient 35 will obtain from using the new ancillary medical procedures. The letter to be sent to the ancillary medical facility 88 instructs the ancillary medical facility that the ancillary medical procedure is discontinued and can also advantageously inform the ancillary medical facility of an amendment to the ancillary medical procedure. The step of discontinuing the ancillary medication also includes providing the physician 27 with a list of "frequently asked questions and answers" so that the physician 27 is prepared for what may be difficult questions posed by the patients 35. This advantageously allows the physician 27 to give the patients 35 clear and concise answers that do not make the patient 35 feel as though the physician 27 and the insurance network 30 are taking advantage of the patient.

The step of providing patient intervention also advantageously includes ordering a new alternative ancillary medical procedure upon a new diagnosis 83. The step of ordering a new ancillary medical procedure advantageously includes providing a monthly update 90 to the physicians 27 regarding new alternative ancillary medical procedures. The monthly updates can come in the form of a newsletter, for example. The step of ordering a new ancillary medical procedure also advantageously includes providing a review 91 between the physician 27 and the healthcare consultation group 25 regarding new ancillary medical procedures and education 92 provided to the physicians 27 and patients 35 regarding the new ancillary medical procedures. The patient's chart is periodically reviewed 93 to ensure that the new ancillary medical procedure is effective and treatment guidelines are provided 94 on a chart insert 48, as illustrated in FIG. 6A.

The methods of managing the healthcare practice 25 and optimizing the profitability of the insurance network 30 also advantageously include updating physicians 27 regarding changes of ancillary medical procedures preferred by the insurance network 30. The step of updating can advantageously include mailing the updated changes to each of the physicians 27 in the [healtheare] *healthcare* provider group 22 using a newsletter, or can advantageously include transmitting the changes to the physicians 27 via electronic mail or flyers, or other types of updates. The step of updating can also advantageously include connecting to a communications network 100 to access the updated information. This advantageously eliminates the time necessary for the physicians 27 to research new preferred ancillary medical procedures. The updates are also a form of continuing education for the physician 27 to learn of new techniques and medications that are available to enhance the treatment of the patients 35.

Some healthcare practices 25 have opted to use personal digital assistants (PDAs) or other electronic data entry and retrieval hardware in their practices. For those groups, whenever possible, the hardware and/or software will be integrated with the information and services provided as described above. Allscripts, Parkstone, and Realtime Rx are just a few examples of companies that sell or lease such equipment. This will be done in an effort to disencumber the physicians 27 so they can focus on better management of their time.

Figure 4:
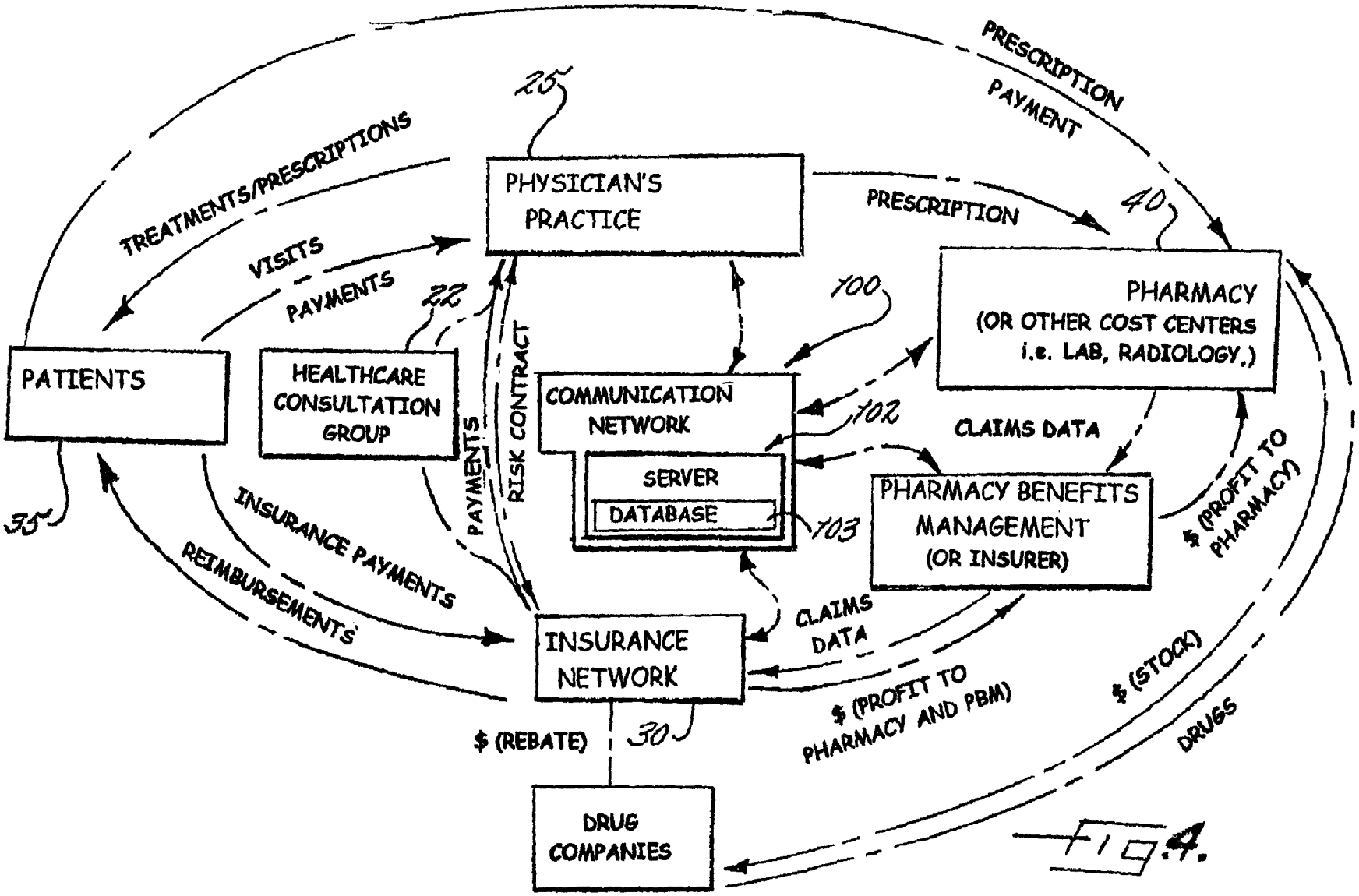
FIG. 4 is a schematic view of a system for a healthcare practice including a plurality of physicians participating in an insurance network according to the present invention.
Figures 5, 6, 6A:
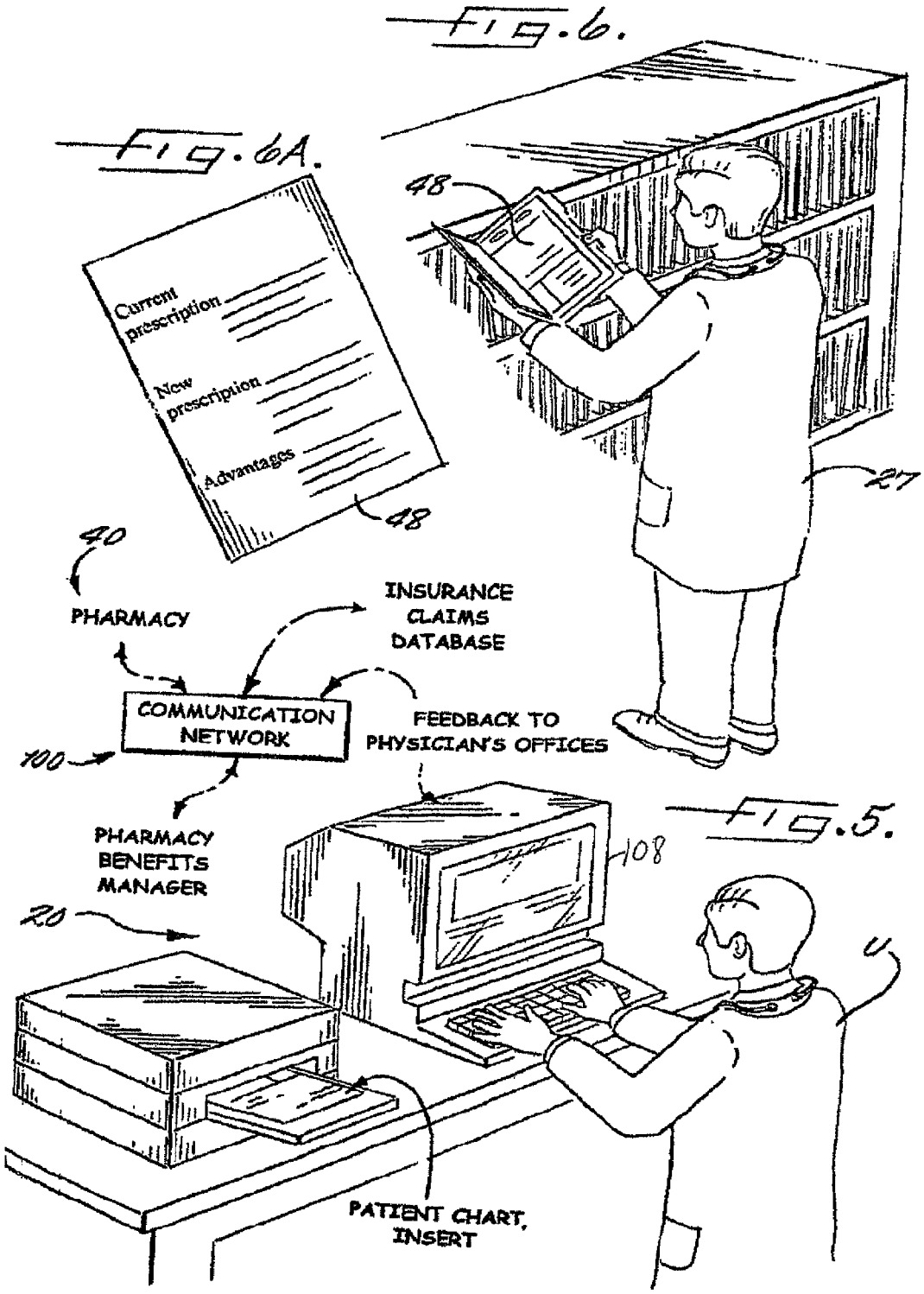
FIG. 5 is an environmental view of a physician accessing a communications network through a user interface of a system for a healthcare practice to obtain information regarding management of ancillary medical costs according to the present invention.
FIG. 6 is an environmental view of a physician researching an information card positioned in a patient's chart to determine if an alternative ancillary medical procedure is appropriate according to the present invention.
FIG. 6A is a front elevational view of an information card that can be positioned in a patient's chart according to the present invention.

As best illustrated in FIGS. 1A, 4, and 5, the present invention advantageously includes a healthcare management optimization system 20 for a healthcare practice 25 including a plurality of physicians 27 participating in an insurance network 30. The system can advantageously include a server 102 with a database 103 and a communications network 100. The system 20 also preferably includes a plurality of computers 108 positioned to be in communication with the communications network 100, each including a user interface responsive to a user. The database 103 can advantageously include first and second databases. The first database includes information regarding preferred ancillary medical procedures of an insurance network. The second database includes ancillary medical costs of a plurality of physicians 27 participating in the insurance network 30. The system further includes an updater positioned on the server 102 and responsive to the user interface for updating each of the plurality of physicians 27 on any changes of preferred ancillary medical procedures preferred by the insurance network 30.

The system 20 of the present invention also includes an analyzer such as provided by software programs stored on a computer or processor, as understood by those skilled in the art, positioned on the server 102 and in communication with the first and second databases for comparing the ancillary medical procedures that are preferred by the insurance network 30 with the ancillary medical costs of the plurality of physicians 27 participating in the insurance network 30. The analyzer advantageously identifies ancillary medical costs of the physicians 27 that are not preferred by the insurance network 30. The analyzer further includes calculating means for calculating an average ancillary medical cost per physician 27 for the healthcare practice 25. The average ancillary medical cost is used to identify the physicians 27 that are in need of assistance to reduce the risk of not receiving the predetermined reimbursement amount for ancillary medical costs from the insurance network 30.

The system 20 still further includes recommending means, e.g., provided by software, as understood by those skilled in the art, positioned on the server 102 and responsive to the user interface, for recommending to each of the plurality of physicians 27 alternative ancillary medical procedures that are preferred by the insurance network 30. The recommending means can advantageously be provided by software that resides on the server 102. The system also preferably includes managing means, e.g., provided by software, as understood by those skilled in the art, for managing ancillary medical cost management behavior of the physicians 27. The managing means can advantageously be provided by software that resides on the server 102. The managing means preferably includes a modifier to modify the management behavior of the physicians 27 so that the physicians 27 engage in ancillary medical procedures that are preferred by the insurance network 30. The managing means also includes an identifier for identifying at least one of the plurality of physicians 27 in the healthcare practice 25 participating in the insurance network 30 that is at a greater risk of not receiving a predetermined reimbursement amount for the ancillary medical costs from the insurance network 30 because of engagement in ancillary medical procedures that are not as profitable to the insurance network 30.

The system 20 of the present invention still further includes patient intervening means, e.g., provided by software, as understood by those skilled in the art, for identifying at least one patient 35 whose present ancillary medical procedures are not preferred by the insurance network 30. The patient intervening means can advantageously be provided by software that resides on the server 102. The management means of the system 20 further includes generating means, e.g., also preferably provided by software, as understood by those skilled in the art, for generating a plurality of letters to modify the ancillary medical procedures of the physician 27. The letters include first and second letters. The first letter informs the ancillary medical facility that the patient's 35 present ancillary medical procedure is modified. The second letter is sent to the patient 35 to inform the patient of the new ancillary medical procedure. The second letter includes educational information informing the patient 35 of the benefits of the new ancillary medical procedure and educational materials that may answer any questions that the patient 27 may have.

As illustrated in FIG. 3, the present invention also provides methods of collecting fees 120 for managing and optimizing the profitability of a plurality of physicians 27 in a healthcare practice 25 and for managing and optimizing the profitability of an insurance network 30. The method includes establishing a relationship 122 between a healthcare consultation group 22, a plurality of physicians 27 in a healthcare practice 25, and an insurance network 30. This advantageously provides a team working towards a common goal, i.e., a team working towards the goal of enhancing profitability through better and more cost-effective healthcare. The newly established relationship can be used to modify the physicians' ancillary medical cost management behavior to enhance the profitability of the insurance network 30 and to reduce the physician's 27 risk of not receiving a predetermined reimbursement amount for ancillary medical costs from the insurance network 30.

The method of collecting fees 120 can advantageously include the step of the healthcare consultation group 22 funding an incentive pool 124 to be paid to the healthcare practice 25, or to the insurance network 30, depending upon who hires the healthcare consultation group 22. The healthcare consultation group 22 only collects a fee if their services to the healthcare practice 25 and the insurance network 30 are successful. Therefore, the fees are only collected on a success-fee basis. In some cases, however, a nominal fee may be charged by the healthcare consultation group 22 before services are performed. The measure of success of the services of the healthcare consultation group 22 is a decrease in healthcare costs of the insurance network 30 and the physicians 27 in the healthcare practice 25 for specific ancillary medical costs. If services of the healthcare consultation group 22, however, do not decrease healthcare costs for the plurality of physicians 27 or the insurance network 30 below a predetermined level over a preselected period of time, the [finds] *funds* in the incentive pool are turned over to the healthcare practice 25 or the insurance network 30, depending on who is the healthcare consultation group's 22 client. This advantageously provides accountability to the healthcare consultation group 22. Accountability will ease the minds of the healthcare practice 25 and insurance network 30 giving the healthcare consultation group 22 a chance to prove that profits can be enhanced.

The method of collecting fees 120 further includes distributing predetermined percentages 126 of savings attributed to the services of the healthcare consultation group 22. As illustrated in FIG. 3, the savings are distributed to the healthcare practice Y, the healthcare consultation group Z, and the insurance network X. For example, the percentages can be 40% to the consultation group. Clearly these percentages can vary depending on the client of the consulting group and an agreement between the parties. This arrangement advantageously allows all involved to gain, including patients, through more cost-effective medical care. The predetermined percentage that is distributed to the healthcare practice Y can advantageously be further distributed 128 in predetermined percentages evenly to the healthcare practice 25 or allocated proportionately according to the savings 129 of each of the plurality of physicians 27 in the healthcare practice 25.

The step of distributing predetermined percentages 126 of savings attributed to the services of the healthcare consultation group 22 can advantageously vary depending on whether the client of the healthcare consultation group 22 is the healthcare practice 25 or the insurance network 30. The distributed percentages can advantageously be equal between the healthcare consultation group 22, the insurance network 30, and the healthcare practice 25. If, for example, the client of the healthcare consultation group 22 is the healthcare practice 25, then the predetermined percentages distributed to the healthcare consultation group 22 and the healthcare practice 25 can be greater than the predetermined percentage of the savings that are distributed to the insurance network 30, e.g., the insurance network 30 may not collect any percentage of the savings. If, however, the client of the healthcare consultation group 22 is the insurance network 30, then the predetermined percentages distributed to the healthcare consultation group 22 and the insurance network 30 can be greater than the predetermined percentage of the savings that are distributed to the healthcare practice 25.

The method of collecting fees can also advantageously include a pricing, billing, or charging structure. The pricing structure of the healthcare consultation group 22 is straight forward. The clients, i.e., the healthcare practice 25 or the insurance network 30, measure their ancillary medical costs, or pharmacy costs for example, on a per-member per-month (PMPM) basis. During a pharmacy assessment, an average PMPM pharmacy cost (baseline PMPM) is calculated using the clients past six months pharmacy claims and membership data. Each month, the current month's average PMPM pharmacy cost is subtracted from baseline PMPM in order to determine the savings realized from the healthcare consultation group's 22 services.

A commission fee can advantageously be calculated on predetermined percentage of the monthly client savings, e.g., 50% of monthly savings, multiplied by the number of patients each month. For example, a sustained $1.00 PMPM savings for a client with 30,000 covered lives would yield to the healthcare consultation group 22 $15,000 per month, for up the duration of the contract. The contract can span between one and three years, for example, or can have a longer duration. The healthcare consultation group 22 can collect a smaller fee percentage for longer contract durations. If the client desires a longer contract duration, the baseline PMPM can advantageously be increased yearly with respect to annual inflation increases of wholesale prescription medication costs. The risk reversal for the client is that if there is no savings any month, the client pays nothing.

The pricing structure can also advantageously include a referral commission, e.g., $0.25, for each covered life, or a percentage of the client's savings for example, provided to the strategic marketing partners. This referral commission compensates for the commissions paid to sales people and people who refer business to the healthcare consultation group 22. Thus, the healthcare consultation group 22 minimizes the marketing budget while advantageously maximizing marketing results.

The application is related to U.S. patent application Ser. No. 09/812,704, now U.S. Pat. No. 7,398,217, titled "Methods and Systems For Healthcare Practice Management" filed on the same date herewith by the same inventors, which is incorporated herein by reference in its entirety.

In the drawings and specification, there has been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

The invention claimed is:

1. A method of collecting fees for managing and optimizing [the] profitability of a plurality of physicians in a healthcare practice participating in an insurance network, the method comprising the steps of:

establishing a relationship between a healthcare consultation group and [the] *a* healthcare practice participating in [the] *an* insurance network to increase [the] *profitability of a* plurality of [physicians' profitability] *physicians in the healthcare practice* by reducing a risk of the healthcare practice not receiving a predetermined reimbursement amount for ancillary medical costs from the insurance network;

funding an incentive pool;

gathering*, by a computer,* data [in a tangible computer medium from] *on* each of the plurality of physicians in the healthcare practice participating in the insurance network including ancillary medical costs respective to the physicians;

modifying behavior of [at least one of] the plurality of physicians in the healthcare practice for management of the ancillary medical costs responsive to the *gathered* data [gathered in the tangible computer medium];

determining*, by the computer,* whether the ancillary medical costs of the plurality of physicians in the healthcare practice have reached a predetermined level [within] *over* a preselected period of time;

paying funds from the funded incentive pool to the healthcare practice participating in the insurance network when the ancillary medical costs of the plurality of physicians in the healthcare practice have not decreased to the preselected level over the preselected period of time; and distributing predetermined percentages of savings attributed to the [modifying] *modified ancillary medical cost management* behavior of the plurality of physicians [ancillary medical cost management if] *when* the ancillary medical costs of the plurality of physicians in the healthcare practice have decreased to the preselected level over the preselected period of time.

2. The method as defined in claim 1, wherein the step of distributing the predetermined percentages of the savings includes dividing the savings into selected percentages between at least two of the healthcare consultation group, the healthcare practice, and the insurance network, and distributing the savings to the at least two of the healthcare consultation group, the healthcare practice, and the insurance network, based on the selected percentages.

3. The method as defined in claim 2, further comprising the step of collecting no fee by the healthcare consultation group if the healthcare practice does not reduce the ancillary medical costs to the preselected level over the predetermined period of time.

4. The method as defined in claim 3, wherein each of the respective predetermined percentages of savings distributed to the healthcare consultation group and the healthcare practice are greater than the predetermined percentage of the savings distributed to the insurance network, and wherein the step of funding the incentive pool includes the healthcare consultation group funding the incentive pool.

5. The method as defined in claim 4, further comprising the step of providing a billing fee structure from the healthcare consultation group wherein the savings are calculated by subtracting current ancillary medical costs from predetermined baseline ancillary medical costs.

6. The method as defined in claim 5, further comprising the step of calculating the billing fee structure for the healthcare consultation group by multiplying a predetermined percentage of the savings by the number of patients participating in the healthcare practice.

7. The method as defined in claim 1, wherein the ancillary medical costs include any costs taken from the group of pharmacy, radiology, laboratory, anesthesiology, occupational therapy, physical therapy, speech therapy, therapeutic radiology, operating room, or emergency room costs.

8. A method of collecting fees for managing a plurality of physicians in a healthcare practice participating in an insurance network, the method comprising the steps of:

establishing a relationship between a healthcare consultation group and [the] *a* healthcare practice participating in [the] *an* insurance network to reduce a risk of the healthcare practice not receiving a predetermined reimbursement amount for ancillary medical costs from the insurance network;

funding an incentive pool;

establishing a plan to pay funds from the funded incentive pool to the healthcare practice participating in the insurance network, wherein the payment of funds occurs in the plan when the ancillary medical costs of [the] *a* plurality of physicians in the healthcare practice do not decrease to a preselected level over a preselected period of time;

gathering, *by a computer,* data [in a tangible computer medium from] *on* each of the plurality of physicians in the healthcare practice participating in the insurance network including ancillary medical costs respective to the physicians;

modifying behavior of [at least one of] the plurality of physicians in the healthcare practice for management of the ancillary medical costs responsive to the *gathered* data [gathered in the tangible computer medium];

determining, *by the computer,* whether the ancillary medical costs of the plurality of physicians in the healthcare practice have reached the preselected level within the preselected period of time; and distributing predetermined percentages of savings attributed to the [modifying] *modified* ancillary medical cost management behavior of the plurality of physicians if the ancillary medical costs have decreased to the preselected level over the preselected period of time.

9. The method as defined in claim 8, wherein the step of funding the incentive pool includes the healthcare consultation group funding the incentive pool, wherein the modifying behavior of the plurality of physicians is responsive to recommendations of the healthcare consultation group, and the method further comprising the step of paying funds from the funded incentive pool only if the ancillary medical costs of the plurality of physicians in the healthcare practice do not decrease to the preselected level over the preselected period of time responsive to the modifying behavior.

10. The method as defined in claim 9, wherein the step of distributing the predetermined percentages of the savings includes dividing the savings into selected percentages between at least two of the healthcare consultation group, the healthcare practice, and the insurance network, and distributing the savings to the at least two of the healthcare consultation group, the healthcare practice, and the insurance network, based on the selected percentages.

11. The method as defined in claim 10, further comprising the steps of collecting no fee by the healthcare consultation group if the healthcare practice does not reduce the ancillary medical costs to the preselected level over the predetermined period of time and providing a billing fee structure from the healthcare consultation group wherein the savings are calculated by subtracting current ancillary medical costs from predetermined baseline ancillary medical costs.

12. The method as defined in claim 11, wherein each of the respective predetermined percentages of savings distributed to the healthcare consultation group and the healthcare practice are greater than the predetermined percentage of the savings distributed to the insurance network, and wherein the ancillary medical costs include any costs taken from the group of pharmacy, radiology, laboratory, anesthesiology, occupational therapy, physical therapy, speech therapy, therapeutic radiology, operating room, or emergency room costs.

13. A method of collecting fees for managing and optimizing the profitability of an insurance network having a plurality of physicians in a healthcare practice participating therein, the method comprising the steps of:

establishing a relationship between a healthcare management consultation group and [the] *a* healthcare practice participating in [the] *an* insurance network to increase the insurance network's profitability by [limiting the plurality of physicians'] *modifying* ancillary medical cost management behavior *of a plurality of physicians in the healthcare practice* that is not preferred by the insurance network;

gathering, *by a computer,* data [in a tangible computer medium from] *on* each of the plurality of physicians in the healthcare practice participating in the insurance network regarding management of ancillary medical costs respective to the physicians;

modifying behavior of [at least one of] the plurality of physicians in the healthcare practice for management of the ancillary medical costs responsive to the *gathered* data [gathered in the tangible computer medium];

determining, *by the computer,* whether the ancillary medical costs of the plurality of physicians in the healthcare practice have reached a preselected level [within] *over* a preselected period of time;

funding an incentive pool to be paid to the insurance network when the modified medical management practices do not decrease ancillary medical costs of the insurance network *related to the ancillary medical costs of the plurality of physicians in the healthcare practice participating in the insurance network* to the preselected level over the preselected period of time; and distributing predetermined percentages of savings attributed to the [modifying] *modified ancillary medical cost management* behavior of the plurality of physicians

[ancillary medical cost management to at least one of] *to one or more of the following:* the insurance network and the healthcare management consultation group, when the ancillary medical costs have decreased to the preselected level over the preselected period of time.

14. The method as defined in claim 13, wherein the step of distributing the predetermined percentages of the savings includes dividing the savings into selected percentages between at least two of the healthcare consultation group, the healthcare practice, and the insurance network, and distributing the savings to the at least two of the healthcare consultation group, the healthcare practice, and the insurance network, based on the selected percentages.

15. The method as defined in claim 14, further comprising the steps of collecting no fee by the healthcare consultation group if the modified medical management practices do not reduce the ancillary medical costs of the insurance network to the preselected level over the predetermined period of time.

16. The method as defined in claim 14, wherein each of the respective predetermined percentages of savings distributed to the healthcare consultation group and the insurance network are greater than the predetermined percentage of the savings distributed to the healthcare practice.

17. The method as defined in claim 16, further comprising the step of providing a billing fee structure from the healthcare consultation group wherein the savings are calculated by subtracting current ancillary medical costs from predetermined ancillary medical costs.

18. The method as defined in claim 17, further comprising the step of calculating the billing fee structure for the healthcare consultation group by multiplying a predetermined percentage of the savings by the number of patients participating in the healthcare practice.

19. The method as defined in claim 13, wherein the ancillary medical costs include any costs taken from the group of pharmacy, radiology, laboratory, anesthesiology, occupational therapy, physical therapy, speech therapy, therapeutic radiology, operating room, or emergency room costs.

*20. A computer-assisted method of collecting fees for managing and enhancing profitability of a plurality of physicians in a healthcare practice participating in an insurance network, the method comprising the steps of:*

*providing a first computer associated with a tangible non-transitory computer readable medium and positioned to receive data indicating management of ancillary medical costs by a plurality of physicians in a healthcare practice participating in an insurance network;*

*establishing an electronic communications network between a healthcare management consultation group and the healthcare practice participating in the insurance network;*

*receiving data by the first computer from at least one other computer associated with the plurality of physicians in the healthcare practice participating in the insurance network, the received data including ancillary medical costs attributed to the plurality of physicians;*

*identifying by the first computer one or more the plurality of physicians in the healthcare practice participating in the insurance network having ancillary medical costs that exceed a certain level to thereby identify one or more of the plurality of physicians in the healthcare practice for behavior modification with respect to ancillary medical costs to increase profitability of the plurality of physicians by reducing a risk of the healthcare practice not receiving a predetermined reimbursement amount for ancillary medical costs from the insurance network;*

*generating information by the first computer identifying recommended alternative ancillary medical procedures to modify the behavior of the plurality of physicians in the healthcare practice with respect to management of the ancillary medical costs;*

*determining by the first computer whether the ancillary medical costs of the plurality of physicians in the healthcare practice have reached a predetermined level over a preselected period of time;*

*funding an incentive pool by the healthcare consultation group to provide for paying funds to the healthcare practice participating in the insurance network when the ancillary medical costs of the plurality of physicians in the healthcare practice have not decreased to the predetermined level over the preselected period of time;*

*performing the step of paying funds from the funded incentive pool to the healthcare practice participating in the insurance network when the ancillary medical costs of the plurality of physicians in the healthcare practice have not decreased to the predetermined level over the preselected period of time;*

*calculating a predetermined percentage of savings attributed to modified ancillary medical cost management behavior of the plurality of physicians with respect to ancillary medical costs; and*

*distributing the predetermined percentage of savings to the healthcare practice participating in the insurance network when the ancillary medical costs of the plurality of physicians in the healthcare practice have decreased to the predetermined level over the preselected period of time.*

*21. A computer-assisted method of collecting fees for managing a plurality of physicians in a healthcare practice participating in an insurance network, the method comprising the steps of:*

*providing a first computer associated with a tangible non-transitory computer readable medium and positioned to receive data indicating management of ancillary medical costs of a plurality of physicians in a healthcare practice participating in an insurance network;*

*establishing an electronic communications network between a healthcare management consultation group and the healthcare practice participating in the insurance network to thereby facilitate communications between the healthcare management consultation group and the healthcare practice;*

*funding an incentive pool to provide for payment of funds under certain conditions;*

*establishing a plan to pay funds from the funded incentive pool to the healthcare practice participating in the insurance network, whereby the payment of funds occurs in the plan when the ancillary medical costs of the plurality of physicians in the healthcare practice do not decrease to a preselected level over a preselected period of time;*

*receiving data by the first computer for each of the plurality of physicians in the healthcare practice participating in the insurance network, the received data including ancillary medical costs attributed to the respective physicians;*

*identifying by the first computer one or more of the plurality of physicians in the healthcare practice participating in the insurance network having ancillary medical costs that exceed a certain level to thereby identify one or more of the plurality of physicians in the healthcare practice for behavior modification with respect to management of ancillary medical costs;*

*generating information identifying recommended alternative ancillary medical procedures by the first computer to modify behavior of the plurality of physicians in the healthcare practice with respect to management of the ancillary medical costs to thereby reduce a risk of the healthcare practice not receiving a predetermined reimbursement amount for ancillary medical costs from the insurance network;*

*determining by the first computer whether the ancillary medical costs of the plurality of physicians in the healthcare practice have reached the preselected level over the preselected period of time;*

*calculating a predetermined percentage of savings attributed to modified ancillary medical cost management behavior of the plurality of physicians; and*

*distributing the predetermined percentage of savings when the ancillary medical costs have decreased to the preselected level over the preselected period of time.*

*22. A computer-assisted method of collecting fees for managing and enhancing profitability of an insurance network including a plurality of physicians in a healthcare practice participating in the insurance network, the method comprising the steps of:*

*providing a first computer associated with a tangible non-transitory computer readable medium and positioned to receive data indicating management of ancillary medical costs of a plurality of physicians in a healthcare practice participating in an insurance network;*

*establishing an electronic communications network between a healthcare management consultation group and the healthcare practice participating in the insurance network;*

*responsive to establishment of the electronic communications network between a healthcare management consultation group and the healthcare practice, receiving data by the first computer from at least one other computer associated with the plurality of physicians, the received data indicating ancillary medical costs attributed to each of the plurality of physicians in the healthcare practice participating in the insurance network;*

*responsive to the received data, identifying by the first computer one or more of the plurality of physicians in the healthcare practice participating in the insurance network having ancillary medical costs that exceed a certain level to thereby identify one or more of the plurality of physicians in the healthcare practice for behavior modification;*

*responsive to identifying one or more of the plurality of physicians in the healthcare practice participating in the insurance network having ancillary medical costs that exceed a certain level, generating information identifying alternative recommended ancillary medical practices by the first computer to modify the behavior of the plurality of physicians in the healthcare practice with respect to management of the ancillary medical costs that is not preferred by the insurance network to thereby reduce ancillary medical costs attributed to the plurality of physicians to increase the insurance network's profitability;*

*determining by the first computer whether the ancillary medical costs of the plurality of physicians in the healthcare practice have reached a preselected level over a preselected period of time;*

*funding an incentive pool by the healthcare consultation group to provide for paying funds to the insurance network when the modified ancillary medical costs management behavior does not decrease ancillary medical costs of the insurance network to the preselected level over the preselected period of time;*

*responsive to the first computer determining whether the ancillary medical costs of the plurality of physicians in the healthcare practice have reached the predetermined level over the preselected period of time, performing the step of paying funds from the funded incentive pool to the insurance network when the modified ancillary medical costs management behavior does not decrease ancillary medical costs of the insurance network to the preselected level over the preselected period of time;*

*responsive to the first computer determining whether the ancillary medical costs of the plurality of physicians in the healthcare practice have reached the predetermined level over the preselected period of time, calculating a predetermined percentage of savings attributed to modified ancillary medical costs management behavior of the plurality of physicians; and*

*distributing the predetermined percentage of savings to one or more of the following: the insurance network and the healthcare management consultation group, when the ancillary medical costs have decreased to the preselected level over the preselected period of time.*

*23. A computer-assisted method of collecting fees for managing and enhancing profitability of a plurality of physicians in a healthcare practice participating in an insurance network, the method comprising the steps of:*

*providing a first computer associated with a tangible non-transitory computer readable medium and positioned to receive data indicating management of ancillary medical costs by a plurality of physicians in a healthcare practice participating in an insurance network;*

*establishing an electronic communications network between a healthcare management consultation group and the healthcare practice participating in the insurance network;*

*responsive to establishment of the electronic communications network between the healthcare management consultation group and the healthcare practice, receiving data by the first computer from at least one other computer associated with the plurality of physicians in the healthcare practice participating in the insurance network, the received data including ancillary medical costs attributed to the plurality of physicians,*

*responsive to the received data, identifying by the first computer one or more of the plurality of physicians in the healthcare practice participating in the insurance network having ancillary medical costs that exceed a certain level to thereby identify one or more of the plurality of physicians in the healthcare practice for behavior modification with respect to ancillary medical costs to increase profitability of the plurality of physicians by reducing a risk of the healthcare practice not receiving a predetermined reimbursement amount for ancillary medical costs from the insurance network;*

*responsive to identifying one or more of the plurality of physicians in the healthcare practice participating in the insurance network having ancillary medical costs that exceed a certain level, generating information by the first computer identifying recommended alternative ancillary medical procedures to modify the behavior of the plurality of physicians in the healthcare practice with respect to management of the ancillary medical costs;*

*determining by the first computer whether the ancillary medical costs of the plurality of physicians in the healthcare practice have reached a predetermined level over a preselected period of time;*

*responsive to a result of the determination of whether the ancillary medical costs of the plurality of physicians in the healthcare practice have reached the predetermined level over the preselected period of time, performing the step of paying funds from a funded incentive pool to the healthcare practice participating in the insurance network when the ancillary medical costs of the plurality of physicians in the healthcare practice have not decreased to the predetermined level over the preselected period of time; and*

*responsive to the result of the determination of whether the ancillary medical costs of the plurality of physicians in the healthcare practice have reached the predetermined level over the preselected period of time, calculating a predetermined percentage of savings attributed to modified ancillary medical cost management behavior of the plurality of physicians with respect to ancillary medical costs; and*

*distributing the predetermined percentage of savings to the healthcare practice participating in the insurance network when the ancillary medical costs of the plurality of physicians in the healthcare practice have decreased to the predetermined level over the preselected period of time.*

*24. A healthcare management system for collecting fees for managing and enhancing profitability of a plurality of physicians in a healthcare practice participating in an insurance network, the system comprising:*

*a computer to facilitate management of a healthcare practice participating in an insurance network, the computer having a tangible storage medium for storing computer executable program code; and*

*computer executable program code to facilitate modifying ancillary medical cost management behavior of a plurality of physicians in the healthcare practice and to facilitate paying a percentage of savings attributed to modified ancillary medical cost management behavior of the plurality of physicians, the computer executable program code stored in the storage medium of the computer and executable by the computer to perform the following operations:*

*establishing communications between the healthcare management consultation group and the healthcare practice participating in the insurance network,*

*responsive to establishment of communications between the healthcare management consultation group and the healthcare practice participating in the insurance network, receiving data from at least one other computer associated with the plurality of physicians in the healthcare practice participating in the insurance network, the received data including data indicating ancillary medical costs attributed to the plurality of physicians,*

*responsive to the received data, identifying one or more of the plurality of physicians in the healthcare practice participating in the insurance network having ancillary medical costs that exceed a certain level to thereby identify one or more of the plurality of physicians in the healthcare practice for behavior modification with respect to ancillary medical costs to increase profitability of the plurality of physicians by reducing a risk of the healthcare practice not receiving a predetermined reimbursement amount for ancillary medical costs from the insurance network,*

*responsive to identifying one or more of the plurality of physicians in the healthcare practice participating in the insurance network having ancillary medical costs that exceed a certain level, generating information identifying recommended alternative ancillary medical procedures to modify the behavior of the plurality of physicians in the healthcare practice with respect to management of the ancillary medical costs,*

*determining whether the ancillary medical costs of the plurality of physicians in the healthcare practice have reached a predetermined level over a preselected period of time,*

*responsive to determining whether the ancillary medical costs of the plurality of physicians in the healthcare practice have reached the predetermined level over the preselected period of time, calculating for distribution to the healthcare practice, a predetermined percentage of savings attributed to the modified ancillary medical cost management behavior of the plurality of physicians, and*

*distributing the predetermined percentage of savings attributed to the modified ancillary medical cost management behavior of the plurality of physicians when the ancillary medical costs of the plurality of physicians in the healthcare practice have decreased to the predetermined level over the preselected period of time; and*

*a funded incentive pool funded by the healthcare consultation group and configured to provide for paying funds to the healthcare practice participating in the insurance network when the ancillary medical costs of the plurality of physicians in the healthcare practice have not decreased to the predetermined level over the preselected period of time.*

*25. A healthcare management system for collecting fees for managing and enhancing profitability of a plurality of physicians in a healthcare practice participating in an insurance network, the system comprising:*

*a computer to facilitate management of a healthcare practice participating in an insurance network, the computer having a tangible storage medium for storing computer executable program code; and*

*computer executable program code to facilitate modifying ancillary medical cost management behavior of a plurality of physicians in the healthcare practice and to facilitate paying a percentage of savings attributed to modified ancillary medical cost management behavior of the plurality of physicians, the computer executable program code stored in the storage medium of the computer and executable by the computer to perform the following operations:*

*establishing communications between a healthcare management consultation group and the healthcare practice participating in the insurance network to thereby facilitate a relationship between the healthcare management consultation group and the healthcare practice,*

*responsive to establishment of communications between the healthcare management consultation group and the healthcare practice participating in the insurance network, receiving data for each of the plurality of physicians in the healthcare practice participating in the insurance network, the received data including data indicating ancillary medical costs attributed to the plurality of physicians,*

*responsive to the received data, identifying by the first computer one or more of the plurality of physicians in the healthcare practice participating in the insurance network having ancillary medical costs that exceed a certain level to thereby identify one or more of the plurality of physicians in the healthcare practice for behavior modification with respect to management of ancillary medical costs,*

*responsive to identifying one or more of the plurality of physicians in the healthcare practice participating in the insurance network having ancillary medical costs that exceed a certain level, generating information identifying recommended alternative ancillary medical procedures to modify behavior of the plurality of physicians in the healthcare practice with respect to management of the ancillary medical costs to thereby reduce a risk of the healthcare practice not receiving a predetermined reimbursement amount for ancillary medical costs from the insurance network,*

*determining whether the ancillary medical costs of the plurality of physicians in the healthcare practice have reached the preselected level over the preselected period of time,*

*responsive to determining whether the ancillary medical costs of the plurality of physicians in the healthcare practice have reached the predetermined level over the preselected period of time, calculating for distribution a predetermined percentage of savings attributed to modified ancillary medical cost management behavior of the plurality of physicians, and*

*distributing the predetermined percentage of savings attributed to the modified ancillary medical cost management behavior of the plurality of physicians when the ancillary medical costs have decreased to the preselected level over the preselected period of time; and*

*a funded incentive pool funded by the healthcare consultation group and configured to provide for paying funds to the healthcare practice participating in the insurance network when the ancillary medical costs of the plurality of physicians in the healthcare practice have not decreased to the predetermined level over the preselected period of time.*

*26. A healthcare management system for collecting fees for managing and enhancing profitability of a plurality of physicians in a healthcare practice participating in an insurance network, the system comprising:*

*a computer to facilitate management of a healthcare practice participating in an insurance network, the computer having a tangible storage medium for storing computer executable program code; and*

*computer executable program code to facilitate modifying ancillary medical cost management behavior of a plurality of physicians in the healthcare practice and to facilitate paying a percentage of savings attributed to modified ancillary medical cost management behavior of the plurality of physicians, the computer executable program code stored in the storage medium of the computer and executable by the computer to perform the following operations:*

*establishing communications between the healthcare management consultation group and the healthcare practice participating in the insurance network,*

*responsive to establishment of communications between the healthcare management consultation group and the healthcare practice participating in the insurance network, receiving data from at least one other computer associated with the plurality of physicians, the received data indicating the ancillary medical costs attributed to each of the plurality of physicians in the healthcare practice participating in the insurance network,*

*responsive to the received data, identifying by the first computer one or more of the plurality of physicians in the healthcare practice participating in the insurance network having ancillary medical costs that exceed a certain level to thereby identify one or more of the plurality of physicians in the healthcare practice for behavior modification,*

*responsive to identifying one or more of the plurality of physicians in the healthcare practice participating in the insurance network having ancillary medical costs that exceed a certain level, generating information identifying alternative recommended ancillary medical practices to modify the behavior of the plurality of physicians in the healthcare practice with respect to management of the ancillary medical costs that is not preferred by the insurance network to thereby reduce ancillary medical costs attributed to the plurality of physicians to increase the insurance network's profitability,*

*determining whether the ancillary medical costs of the plurality of physicians in the healthcare practice have reached a preselected level over a preselected period of time,*

*responsive to determining whether the ancillary medical costs of the plurality of physicians in the healthcare practice have reached the predetermined level within the preselected period of time, calculating for distribution to one or more of the following: the insurance network and the healthcare management consultation group, a predetermined percentage of savings attributed to modified ancillary medical costs management behavior of the plurality of physicians, and*

*distributing the predetermined percentage of savings attributed to the modified ancillary medical cost management behavior of the plurality of physicians when the ancillary medical costs have decreased to the preselected level over the preselected period of time; and*

*a funded incentive pool funded by the healthcare consultation group and configured to provide for paying funds to the insurance network when the modified ancillary medical costs management behavior does not decrease ancillary medical costs of the insurance network to the preselected level over the preselected period of time.*

* * * * *